US012059238B2

United States Patent
Saroka et al.

(10) Patent No.: US 12,059,238 B2
(45) Date of Patent: *Aug. 13, 2024

(54) METHOD, SYSTEM AND APPARATUS FOR USING ELECTROMAGNETIC RADIATION FOR MONITORING A TISSUE OF A USER

(71) Applicant: Sensible Medical Innovations Ltd., Netanya (IL)

(72) Inventors: Amir Saroka, Herzlia (IL); Shlomi Bergida, Ein Sarid (IL); Nadav Mizrahi, Tel-Aviv (IL); Dan Rappaport, Tel-Aviv (IL); Amir Ronen, Ramot Menashe (IL); Benyamin Almog, Kibbutz Givat Brenner (IL)

(73) Assignee: Sensible Medical Innovations Ltd., Netanya (IL)

( * ) Notice: Subject to any disclaimer, the term of this patent is extended or adjusted under 35 U.S.C. 154(b) by 116 days.

This patent is subject to a terminal disclaimer.

(21) Appl. No.: 17/007,005

(22) Filed: Aug. 31, 2020

(65) Prior Publication Data

US 2020/0397333 A1 Dec. 24, 2020

Related U.S. Application Data

(63) Continuation of application No. 13/922,299, filed on Jun. 20, 2013, now Pat. No. 10,758,150, which is a
(Continued)

(51) Int. Cl.
*A61B 5/05* (2021.01)
*A61B 5/00* (2006.01)

(52) U.S. Cl.
CPC .............. *A61B 5/05* (2013.01); *A61B 5/00* (2013.01); *A61B 5/7203* (2013.01); *A61B 5/726* (2013.01); *A61B 5/7264* (2013.01); *A61B 5/7275* (2013.01)

(58) Field of Classification Search
None
See application file for complete search history.

(56) References Cited

U.S. PATENT DOCUMENTS

| 3,534,727 A | 10/1970 | Roman |
| 4,016,868 A | 4/1977 | Allison |

(Continued)

FOREIGN PATENT DOCUMENTS

| CA | 2898342 | 7/2014 |
| EP | 0694282 | 1/1996 |

(Continued)

OTHER PUBLICATIONS

Official Action Dated Mar. 31, 2022 from US Patent and Trademark Office Re. U.S. Appl. No. 16/888,921. (54 pages).
(Continued)

*Primary Examiner* — Katherine L Fernandez

(57) ABSTRACT

A wearable monitoring apparatus for monitoring at least one biological parameter of an internal tissue of an ambulatory user. Said wearable monitoring apparatus comprises at least one transducer configured for delivering electromagnetic (EM) radiation to said internal tissue and intercepting a reflection of said EM radiation said reform in a plurality of transmission sessions during at least 24 hours, a processing unit configured for analyzing respective said reflection and identifying a change in said at least one biological parameter accordingly, a reporting unit configured for generating a report according to said change, and a housing for containing said at least one transducer, said reporting unit, and said processing unit, said housing being configured for being disposed on said body of said ambulatory user.

21 Claims, 8 Drawing Sheets

Related U.S. Application Data continuation of application No. 12/676,385, filed as application No. PCT/IL2008/001198 on Sep. 4, 2008, now abandoned.

(60) Provisional application No. 60/969,966, filed on Sep. 5, 2007, provisional application No. 60/969,965, filed on Sep. 5, 2007, provisional application No. 60/969,963, filed on Sep. 5, 2007.

(56) References Cited

U.S. PATENT DOCUMENTS

| | | | |
|---|---|---|---|
| 4,240,445 A | 12/1980 | Iskander et al. | |
| 4,279,257 A | 7/1981 | Hochstein | |
| 4,381,510 A | 4/1983 | Wren | |
| 4,488,559 A | 12/1984 | Iskander | |
| 4,572,197 A | 2/1986 | Moore et al. | |
| 4,580,572 A | 4/1986 | Granek et al. | |
| 4,647,281 A | 3/1987 | Carr | |
| 4,676,252 A | 6/1987 | Trautman et al. | |
| 4,690,149 A | 9/1987 | Ko | |
| 4,877,034 A | 10/1989 | Atkins et al. | |
| 4,920,969 A | 5/1990 | Suzuki et al. | |
| 4,926,868 A | 5/1990 | Larsen | |
| 4,958,638 A | 9/1990 | Sharpe et al. | |
| 4,991,585 A * | 2/1991 | Mawhinney | A61B 5/0507 600/534 |
| 5,002,060 A * | 3/1991 | Nedivi | A61B 5/0205 310/329 |
| 5,078,134 A | 1/1992 | Heilman et al. | |
| 5,132,623 A | 7/1992 | De et al. | |
| 5,282,840 A | 2/1994 | Hudrlik | |
| 5,334,141 A | 8/1994 | Carr et al. | |
| 5,363,050 A | 11/1994 | Guo et al. | |
| 5,394,882 A * | 3/1995 | Mawhinney | A61B 5/0002 128/903 |
| 5,479,120 A | 12/1995 | McEwan | |
| 5,517,198 A | 5/1996 | McEwan | |
| 5,523,760 A | 6/1996 | McEwan | |
| 5,563,605 A | 10/1996 | McEwan | |
| 5,573,012 A | 11/1996 | McEwan | |
| 5,576,627 A | 11/1996 | McEwan | |
| 5,604,531 A | 2/1997 | Iddan et al. | |
| 5,728,143 A | 3/1998 | Gough et al. | |
| 5,738,102 A | 4/1998 | Lemelson | |
| 5,749,369 A | 5/1998 | Rabinovich et al. | |
| 5,766,208 A | 6/1998 | McEwan | |
| 5,804,921 A | 9/1998 | McEwan et al. | |
| 5,805,110 A | 9/1998 | McEwan | |
| 5,807,257 A | 9/1998 | Bridges | |
| 5,829,437 A | 11/1998 | Bridges | |
| 5,833,711 A | 11/1998 | Schneider, Sr. | |
| 5,861,019 A | 1/1999 | Sun et al. | |
| 5,876,353 A | 3/1999 | Riff | |
| 5,883,591 A | 3/1999 | McEwan | |
| 5,947,910 A | 9/1999 | Zimmet | |
| 5,957,861 A | 9/1999 | Combs et al. | |
| 5,964,703 A | 10/1999 | Goodman et al. | |
| 5,995,863 A | 11/1999 | Farace et al. | |
| 6,015,386 A | 1/2000 | Kensey et al. | |
| 6,026,173 A | 2/2000 | Svenson et al. | |
| 6,061,589 A * | 5/2000 | Bridges | A61B 6/0435 600/430 |
| 6,064,903 A | 5/2000 | Riechers et al. | |
| 6,111,415 A | 8/2000 | Moshe | |
| 6,169,925 B1 | 1/2001 | Villaseca et al. | |
| 6,211,663 B1 | 4/2001 | Moulthrop et al. | |
| 6,233,479 B1 | 5/2001 | Haddad et al. | |
| 6,236,889 B1 | 5/2001 | Soykan et al. | |
| 6,281,843 B1 | 8/2001 | Evtioushkine et al. | |
| 6,330,479 B1 | 12/2001 | Stauffer | |
| 6,332,087 B1 | 12/2001 | Svenson et al. | |
| 6,332,091 B1 | 12/2001 | Burns et al. | |
| 6,351,246 B1 | 2/2002 | McCorkle | |
| 6,417,797 B1 | 7/2002 | Cousins et al. | |
| 6,425,878 B1 | 7/2002 | Shekalim | |
| 6,459,931 B1 | 10/2002 | Hirschman | |
| 6,484,047 B1 | 11/2002 | Vilsmeier | |
| 6,487,428 B1 | 11/2002 | Culver et al. | |
| 6,488,677 B1 | 12/2002 | Bowman et al. | |
| 6,494,829 B1 | 12/2002 | New, Jr. et al. | |
| 6,496,711 B1 | 12/2002 | Athan et al. | |
| 6,512,949 B1 | 1/2003 | Combs et al. | |
| 6,551,252 B2 | 4/2003 | Sackner et al. | |
| 6,574,510 B2 | 6/2003 | Von Arx et al. | |
| 6,577,709 B2 | 6/2003 | Tarr | |
| 6,590,545 B2 | 7/2003 | McCorkle | |
| 6,675,045 B2 | 1/2004 | Mass et al. | |
| 6,682,480 B1 | 1/2004 | Habib et al. | |
| 6,687,523 B1 | 2/2004 | Jayaramen et al. | |
| 6,746,404 B2 | 6/2004 | Schwartz | |
| 6,766,201 B2 | 7/2004 | Von Arx et al. | |
| 6,770,070 B1 | 8/2004 | Balbierz | |
| 6,783,499 B2 | 8/2004 | Schwartz | |
| 6,788,262 B1 | 9/2004 | Adams et al. | |
| 6,802,811 B1 | 10/2004 | Slepian | |
| 6,809,701 B2 | 10/2004 | Amundson et al. | |
| 6,849,046 B1 | 2/2005 | Eyal-Bickels et al. | |
| 6,909,397 B1 | 6/2005 | Greneker III et al. | |
| 6,917,833 B2 | 7/2005 | Denker et al. | |
| 6,954,673 B2 | 10/2005 | Von Arx et al. | |
| 6,972,725 B1 | 12/2005 | Adams | |
| 7,006,856 B2 | 2/2006 | Baker, Jr. et al. | |
| 7,024,248 B2 | 4/2006 | Penner et al. | |
| 7,047,058 B1 | 5/2006 | Dvorsky et al. | |
| 7,072,718 B2 | 7/2006 | Von Arx et al. | |
| 7,077,810 B2 | 7/2006 | Lange et al. | |
| 7,110,823 B2 | 9/2006 | Whitehurst et al. | |
| 7,116,276 B2 | 10/2006 | Lee | |
| 7,122,012 B2 | 10/2006 | Bouton et al. | |
| 7,135,871 B1 | 11/2006 | Pelletier | |
| 7,229,415 B2 | 6/2007 | Schwartz | |
| 7,228,047 B1 | 7/2007 | Szilagyi et al. | |
| 7,315,170 B2 | 1/2008 | Sakayori | |
| 7,316,658 B2 | 1/2008 | Gagne | |
| 7,330,034 B1 | 2/2008 | Pelletier et al. | |
| 7,387,610 B2 | 6/2008 | Stahmann et al. | |
| 7,445,605 B2 | 11/2008 | Overall et al. | |
| 7,450,077 B2 | 11/2008 | Waterhouse et al. | |
| 7,483,752 B2 | 1/2009 | Von Arx et al. | |
| 7,561,908 B2 | 7/2009 | Glukhovsky et al. | |
| 7,591,792 B2 | 9/2009 | Bouton | |
| 7,613,522 B2 | 11/2009 | Christman et al. | |
| 7,628,757 B1 | 12/2009 | Koh | |
| 7,674,244 B2 | 3/2010 | Kalafut et al. | |
| 7,686,762 B1 | 3/2010 | Najafi et al. | |
| 7,725,150 B2 | 5/2010 | Tupin, Jr. et al. | |
| 7,729,776 B2 | 6/2010 | Von Arx et al. | |
| 7,736,309 B2 | 6/2010 | Miller et al. | |
| 7,756,587 B2 | 7/2010 | Penner et al. | |
| 7,825,667 B2 | 11/2010 | Fang et al. | |
| 7,837,629 B2 | 11/2010 | Bardy | |
| 7,844,341 B2 | 11/2010 | Von Arx et al. | |
| 7,860,574 B2 | 12/2010 | Von Arx et al. | |
| 7,872,613 B2 | 1/2011 | Keilman et al. | |
| 8,032,199 B2 | 10/2011 | Linti et al. | |
| 8,235,949 B2 | 8/2012 | Hack et al. | |
| 10,506,943 B2 | 12/2019 | Kochba et al. | |
| 11,564,586 B2 | 1/2023 | Rapport et al. | |
| 2003/0036674 A1 | 2/2003 | Bouton | |
| 2003/0036713 A1* | 2/2003 | Bouton | A61B 5/411 600/587 |
| 2003/0128808 A1 | 7/2003 | Kindlein et al. | |
| 2004/0006279 A1 | 1/2004 | Arad (Abboud) | |
| 2004/0073093 A1* | 4/2004 | Hatlestad | A61B 5/1116 600/300 |
| 2004/0148021 A1 | 7/2004 | Cartledge et al. | |
| 2004/0186395 A1 | 9/2004 | Vastano | |
| 2004/0220632 A1* | 11/2004 | Burnes | A61B 5/366 607/9 |
| 2004/0249257 A1 | 12/2004 | Tupin, Jr. et al. | |
| 2004/0249258 A1 | 12/2004 | Tupin, Jr. et al. | |
| 2004/0254457 A1 | 12/2004 | Van der Weide | |
| 2005/0065567 A1 | 3/2005 | Lee et al. | |

(56) References Cited

U.S. PATENT DOCUMENTS

| | | | |
|---|---|---|---|
| 2005/0107719 A1* | 5/2005 | Arad (Abbound) | A61B 5/0536 600/547 |
| 2005/0124908 A1 | 6/2005 | Belalcazar et al. | |
| 2005/0149139 A1 | 7/2005 | Plicchi et al. | |
| 2005/0171396 A1 | 8/2005 | Pankratov et al. | |
| 2005/0177061 A1 | 8/2005 | Alanen et al. | |
| 2006/0058606 A1 | 3/2006 | Davis et al. | |
| 2006/0235289 A1 | 10/2006 | Wesselink et al. | |
| 2006/0258952 A1 | 11/2006 | Stahmann et al. | |
| 2006/0293609 A1 | 12/2006 | Stahmann et al. | |
| 2007/0032749 A1 | 2/2007 | Overall et al. | |
| 2007/0066904 A1 | 3/2007 | Wiesmann et al. | |
| 2007/0088221 A1 | 4/2007 | Stahmann | |
| 2007/0123770 A1 | 5/2007 | Bouton et al. | |
| 2007/0163584 A1 | 7/2007 | Bohm et al. | |
| 2007/0197878 A1 | 8/2007 | Shklarski | |
| 2007/0238914 A1 | 10/2007 | Royality et al. | |
| 2008/0097530 A1 | 4/2008 | Muccio et al. | |
| 2008/0103440 A1 | 5/2008 | Ferren et al. | |
| 2008/0200802 A1 | 8/2008 | Bhavaraju et al. | |
| 2008/0200803 A1 | 8/2008 | Kwon et al. | |
| 2008/0224688 A1 | 9/2008 | Rubinsky et al. | |
| 2008/0269589 A1 | 10/2008 | Thijs et al. | |
| 2008/0283290 A1 | 11/2008 | Niino et al. | |
| 2008/0288028 A1 | 11/2008 | Larson et al. | |
| 2009/0043223 A1 | 2/2009 | Zhang et al. | |
| 2009/0149918 A1 | 6/2009 | Krulevitch et al. | |
| 2009/0227882 A1 | 9/2009 | Foo | |
| 2009/0228001 A1 | 9/2009 | Pacey | |
| 2009/0228075 A1 | 9/2009 | Dion | |
| 2009/0241972 A1 | 10/2009 | Keilman et al. | |
| 2009/0248129 A1 | 10/2009 | Keilman et al. | |
| 2010/0056907 A1 | 3/2010 | Rappaport et al. | |
| 2010/0256462 A1 | 10/2010 | Rappaport et al. | |
| 2011/0025295 A1 | 2/2011 | Saroka et al. | |
| 2011/0319746 A1 | 12/2011 | Kochba et al. | |
| 2013/0281800 A1 | 10/2013 | Saroka et al. | |
| 2017/0156626 A1 | 6/2017 | Kochba et al. | |
| 2020/0113475 A1 | 4/2020 | Kochba et al. | |
| 2020/0178837 A1 | 6/2020 | Rappaport et al. | |
| 2023/0277079 A1 | 9/2023 | Kochba et al. | |

FOREIGN PATENT DOCUMENTS

| | | |
|---|---|---|
| EP | 1600892 | 11/2005 |
| JP | 2004-528864 | 9/2004 |
| JP | 2005-531386 | 10/2005 |
| JP | 2005-334298 | 12/2005 |
| JP | 2007-509353 | 4/2007 |
| WO | WO 99/39728 | 8/1999 |
| WO | WO 00/71207 | 11/2000 |
| WO | WO 02/053228 | 7/2002 |
| WO | WO 03/009753 | 2/2003 |
| WO | WO 2004/004539 | 1/2004 |
| WO | WO 2005/043100 | 5/2005 |
| WO | WO 2005/074361 | 8/2005 |
| WO | WO 2005/094369 | 10/2005 |
| WO | WO 2007/010460 | 1/2007 |
| WO | WO 2007/055491 | 5/2007 |
| WO | WO 2008/002251 | 1/2008 |
| WO | WO 2008/122056 | 10/2008 |
| WO | WO 2009/031149 | 3/2009 |
| WO | WO 2009/031150 | 3/2009 |
| WO | WO 2011/141915 | 11/2011 |

OTHER PUBLICATIONS

Official Action Dated Jun. 24, 2022 from US Patent and Trademark Office Re. U.S. Appl. No. 16/714,869. (47 pages).
Official Action Dated Mar. 17, 2022 from US Patent and Trademark Office Re. U.S. Appl. No. 16/792,357. (26 pages).
Advisory Action Before the Filing of An Appeal Brief Dated Mar. 2, 2016 From the US Patent and Trademark Office Re. U.S. Appl. No. 12/676,381.
Advisory Action Before the Filing of An Appeal Brief Dated Jun. 6, 2013 From the US Patent and Trademark Office Re. U.S. Appl. No. 12/676,385.
Advisory Action Before the Filing of An Appeal Brief Dated Mar. 18, 2015 From the US Patent and Trademark Office Re. U.S. Appl. No. 12/544,314.
Advisory Action Before the Filing of An Appeal Brief Dated Oct. 21, 2015 From the US Patent and Trademark Office Re. U.S. Appl. No. 13/254,852.
Advisory Action Before the Filing of An Appeal Brief Dated Apr. 22, 2014 From the US Patent and Trademark Office Re. U.S. Appl. No. 13/254,852.
Advisory Action Before the Filing of An Appeal Brief Dated Jul. 25, 2019 From the US Patent and Trademark Office Re. U.S. Appl. No. 12/544,314. (3 pages).
Applicant-Initiated Interview Summary Dated Jul. 2, 2013 From the US Patent and Trademark Office Re. U.S. Appl. No. 12/676,381.
Applicant-Initiated Interview Summary Dated Feb. 5, 2019 From the US Patent and Trademark Office Re. U.S. Appl. No. 12/676,381. (4 pages).
Applicant-Initiated Interview Summary Dated Dec. 11, 2013 From the US Patent and Trademark Office Re. U.S. Appl. No. 12/544,314.
Applicant-Initiated Interview Summary Dated Jun. 13, 2013 From the US Patent and Trademark Office Re. U.S. Appl. No. 12/676,385.
Applicant-Initiated Interview Summary Dated May 16, 2014 From the US Patent and Trademark Office Re. U.S. Appl. No. 13/254,852.
Applicant-Initiated Interview Summary Dated Feb. 20, 2015 From the US Patent and Trademark Office Re. U.S. Appl. No. 13/254,852.
Communication Pursuant to Article 94(3) EPC Dated Aug. 4, 2014 From the European Patent Office Re. Application No. 08808013.0.
Communication Pursuant to Article 94(3) EPC Dated Sep. 27, 2013 From the European Patent Office Re. Application No. 08808013.0.
Communication Pursuant to Article 94(3) EPC Dated Oct. 1, 2019 From the European Patent Office Re. Application No. 17020594.2. (3 Pages).
Communication Pursuant to Article 94(3) EPC Dated May 6, 2013 From the European Patent Office Re. Application No. 10712583.3.
Communication Pursuant to Article 94(3) EPC Dated May 11, 2020 From the European Patent Office Re. Application No. 17020594.2. (3 Pages).
Communication Pursuant to Article 94(3) EPC Dated Apr. 16, 2015 From the European Patent Office Re. Application No. 10712583.3.
Communication Pursuant to Article 94(3) EPC Dated Dec. 17, 2018 From the European Patent Office Re. Application No. 17153865.5. (6 Pages).
Communication Pursuant to Article 94(3) EPC Dated May 18, 2018 From the European Patent Office Re. Application No. 17153865.5. (4 Pages).
Communication Pursuant to Article 94(3) EPC Dated Feb. 19, 2016 From the European Patent Office Re. Application No. 08789867.2.
Communication Pursuant to Article 94(3) EPC Dated Mar. 19, 2014 From the European Patent Office Re. Application No. 08789867.2.
Communication Pursuant to Article 94(3) EPC Dated May 22, 2014 From the European Patent Office Re. Application No. 10712583.3.
Communication Pursuant to Article 94(3) EPC Dated Apr. 29, 2015 From the European Patent Office Re. Application No. 08789867.2.
Communication Pursuant to Article 94(3) EPC Dated Oct. 29, 2013 From the European Patent Office Re. Application No. 08789867.2.
Communication Pursuant to Article 94(3) EPC Dated Sep. 30, 2019 From the European Patent Office Re. Application No. 17153865.5. (4 Pages).
European Search Report and the European Search Opinion Dated Apr. 3, 2017 From the European Patent Office Re. Application No. 17153865.5. (7 Pages).
European Search Report and the European Search Opinion Dated Sep. 20, 2018 From the European Patent Office Re. Application No. 17020594.2. (7 Pages).
Examiner-Initiated Interview Summary Dated Feb. 4, 2016 From the US Patent and Trademark Office Re. U.S. Appl. No. 12/676,381.

(56) References Cited

OTHER PUBLICATIONS

International Preliminary Report on Patentability Dated Sep. 15, 2011 From the International Bureau of WIPO Re. Application No. PCT/IL2010/000182.
International Preliminary Report on Patentability Dated Mar. 18, 2010 From the International Bureau of WIPO Re. Application No. PCT/IL2008/001198.
International Preliminary Report on Patentability Dated Mar. 18, 2010 From the International Bureau of WIPO Re. Application No. PCT/IL2008/001199.
International Search Report and the Written Opinion Dated Jun. 15, 2010 From the International Searching Authority Re. Application No. PCT/IL2010/000182.
International Search Report Dated Feb. 4, 2009 From the International Searching Authority Re. Application No. PCT/IL2008/001198.
International Search Report Dated Jan. 23, 2009 From the International Searching Authority Re. Application No. PCT/IL2008/001199.
Interview Summary Dated Jun. 8, 2017 From the US Patent and Trademark Office Re. U.S. Appl. No. 13/922,299. (3 pages).
Notice of Reason for Rejection Dated Oct. 23, 2015 From the Japanese Patent Office Re. Application No. 2015-000023 and Its Translation Into English.
Notice of Reason for Rejection Dated Jan. 31, 2014 From the Japanese Patent Office Re. Application No. 2010-523644 and Its Translation Into English.
Office Action Dated Jun. 5, 2013 From the Israel Patent Office Re. Application No. 214973 and Its Translation Into English.
Office Action Dated Dec. 14, 2015 From the Israel Patent Office Re. Application No. 239240 and Its Translation Into English.
Office Action Dated Apr. 28, 2014 From the Israel Patent Office Re. Application No. 214973 and Its Translation Into English.
Official Action Dated Jul. 1, 2014 From the US Patent and Trademark Office Re. U.S. Appl. No. 12/676,381.
Official Action Dated Aug. 2, 2018 From the US Patent and Trademark Office Re. U.S. Appl. No. 12/676,381. (19 pages).
Official Action Dated Oct. 2, 2015 From the US Patent and Trademark Office Re. U.S. Appl. No. 13/922,299.
Official Action Dated Jan. 3, 2019 From the US Patent and Trademark Office Re. U.S. Appl. No. 12/676,381. (14 pages).
Official Action Dated Nov. 3, 2014 From the US Patent and Trademark Office Re. U.S. Appl. No. 12/544,314.
Official Action Dated Apr. 4, 2012 From the US Patent and Trademark Office Re. U.S. Appl. No. 12/676,385.
Official Action Dated Apr. 4, 2018 From the US Patent and Trademark Office Re. U.S. Appl. No. 12/544,314. (22 pages).
Official Action Dated Jun. 4, 2018 From the US Patent and Trademark Office Re. U.S. Appl. No. 15/436,902. (44 pages).
Official Action Dated Sep. 4, 2014 From the US Patent and Trademark Office Re. U.S. Appl. No. 13/254,852.
Official Action Dated Jul. 5, 2013 From the US Patent and Trademark Office Re. U.S. Appl. No. 12/846,861.
Official Action Dated Apr. 7, 2017 From the US Patent and Trademark Office Re. U.S. Appl. No. 15/436,902. (41 Pages).
Official Action Dated May 7, 2015 From the US Patent and Trademark Office Re. U.S. Appl. No. 12/676,381.
Official Action Dated Oct. 7, 2015 From the US Patent and Trademark Office Re. U.S. Appl. No. 12/676,381.
Official Action Dated Feb. 8, 2013 From the US Patent and Trademark Office Re. U.S. Appl. No. 12/676,381.
Official Action Dated Mar. 9, 2017 From the US Patent and Trademark Office Re. U.S. Appl. No. 13/922,299. (40 pages).
Official Action Dated Aug. 10, 2017 From the US Patent and Trademark Office Re. U.S. Appl. No. 13/922,299. (26 pages).
Official Action Dated Jun. 10, 2015 From the US Patent and Trademark Office Re. U.S. Appl. No. 13/254,852.
Official Action Dated Apr. 11, 2016 From the US Patent and Trademark Office Re. U.S. Appl. No. 12/676,381.
Official Action Dated Mar. 11, 2014 From the US Patent and Trademark Office Re. U.S. Appl. No. 12/544,314.
Official Action Dated Oct. 11, 2013 From the US Patent and Trademark Office Re. U.S. Appl. No. 12/544,314.
Official Action Dated Dec. 12, 2013 From the US Patent and Trademark Office Re. U.S. Appl. No. 13/254,852.
Official Action Dated Jul. 13, 2016 From the US Patent and Trademark Office Re. U.S. Appl. No. 12/544,314.
Official Action Dated Sep. 13, 2012 From the US Patent and Trademark Office Re. U.S. Appl. No. 12/676,381.
Official Action Dated Mar. 14, 2016 From the US Patent and Trademark Office Re. U.S. Appl. No. 13/254,852.
Official Action Dated Mar. 15, 2019 From the US Patent and Trademark Office Re. U.S. Appl. No. 12/544,314. (5 Pages).
Official Action Dated Oct. 15, 2012 From the US Patent and Trademark Office Re. U.S. Appl. No. 12/846,861.
Official Action Dated Apr. 16, 2019 From the US Patent and Trademark Office Re. U.S. Appl. No. 15/436,902. (27 pages).
Official Action Dated Nov. 16, 2017 From the US Patent and Trademark Office Re. U.S. Appl. No. 15/436,902. (45 pages).
Official Action Dated Dec. 19, 2012 From the US Patent and Trademark Office Re. U.S. Appl. No. 12/544,314.
Official Action Dated Dec. 20, 2012 From the US Patent and Trademark Office Re. U.S. Appl. No. 12/676,385.
Official Action Dated Aug. 21, 2019 From the US Patent and Trademark Office Re. U.S. Appl. No. 13/922,299. (35 pages).
Official Action Dated Oct. 22, 2013 From the US Patent and Trademark Office Re. U.S. Appl. No. 12/676,381.
Official Action Dated Mar. 25, 2013 From the US Patent and Trademark Office Re. U.S. Appl. No. 13/254,852.
Official Action Dated May 25, 2016 From the US Patent and Trademark Office Re. U.S. Appl. No. 13/922,299.
Official Action Dated May 25, 2017 From the US Patent and Trademark Office Re. U.S. Appl. No. 12/544,314. (33 pages).
Official Action Dated Sep. 25, 2015 From the US Patent and Trademark Office Re. U.S. Appl. No. 12/544,314.
Official Action Dated Feb. 26, 2014 From the US Patent and Trademark Office Re. U.S. Appl. No. 12/846,861.
Official Action Dated Dec. 27, 2016 From the US Patent and Trademark Office Re. U.S. Appl. No. 12/676,381. (37 pages).
Official Action Dated Dec. 28, 2017 From the US Patent and Trademark Office Re. U.S. Appl. No. 12/676,381. (23 pages).
Official Action Dated Jun. 29, 2018 From the US Patent and Trademark Office Re. U.S. Appl. No. 13/922,299. (27 pages).
Restriction Official Action Dated Jul. 2, 2015 From the US Patent and Trademark Office Re. U.S. Appl. No. 13/922,299.
Restriction Official Action Dated Jun. 7, 2012 From the US Patent and Trademark Office Re. U.S. Appl. No. 12/544,314.
Summons to Attend Oral Proceedings Pursuant to Rule 115(1) EPC Dated Mar. 16, 2016 From the European Patent Office Re. Application No. 10712583.3.
Summons to Attend Oral Proceedings Pursuant to Rule 115(1) EPC Dated Dec. 23, 2016 From the European Patent Office Re. Application No. 08789867.2. (4 Pages).
Supplementary European Search Report and the European Search Opinion Dated Feb. 13, 2013 From the European Patent Office Re. Application No. 08789867.2.
Supplementary European Search Report and the European Search Opinion Dated Feb. 14, 2013 From the European Patent Office Re. Application No. 08808013.0.
Translation of Notice of Reason for Rejection Dated Sep. 24, 2013 From the Japanese Patent Office Re. Application No. 2010-523644.
Translation of Reason for Rejection Dated Jul. 29, 2016 From the Japanese Patent Office Re. Application No. 2015-000023.
Written Opinion Dated Feb. 4, 2009 From the International Searching Authority Re. Application No. PCT/IL2008/001198.
Written Opinion Dated Jan. 23, 2009 From the International Searching Authority Re. Application No. PCT/IL2008/001199.
Azevedo et al "Micropower Impulse Radar", Science & Technologies Review, Feb. 17-29, 1996.

(56) References Cited

OTHER PUBLICATIONS

Billich "Bio-Medical Sensing Using Ultra Wideband Communications And Radar Technology", PhD Proposal, Department of Information and Telecommunication Technology—University of Trento, Italy—Jan. 2006 (10 pages).
Fear et al. "Enhancing Breast Tumor Detection With Near-Field Imaging", IEEE Microwave Magazine, pp. 48-56, Mar. 2002.
Fear et al. "Microwaves for Breast Cancer Detection", IEEE Potentials, 22(1): 12-18, Feb. 25, 2003.
Gabriel "Compilation of the Dielectric Properties of Body Tissues at RF and Microwave Frequencies", Final Technical Report for the Period Sep. 15, 1993 to Dec. 14, 1994, p. 1-21, Jan. 1996.
Gentili et al "A Versatile Microwave Plethysmograph for The Monitoring Of Physiological Parameters", IEEE Transactions On Biomedical Engineering 49(10) 1204-1210, Oct. 2002.
Hill-Rom "The Vest® Airway Clearance System. Information for Physicians", Hill-Rom, Retrieved From the Internet, 3 P., Nov. 24, 2011.
Iskander et al. A Microwave Method for Measuring Changes in Lung Water Content: Numerical Simulation, IEEE Transactions on Biomedical Engineering 28(12): 797-804, Dec. 1981.
Jafari et al. "Ultrawideband Radar Imagingn System for Biomedical Applications", Journal of Vacuum Science and Technology A: Vacuum, Surfaces, and Films, 24(3): 752-757, May/Jun. 2006.
Jiang et al. "Ultrasound-Guided Microwave Imaging of Breast Cancer: Tissue Phantom and Pilot Clinical Experiments", Medical Physics, 32(8): 2528-2535, Aug. 2005.
Juweid et al. "Positron-Emission Tomography and Assessment of Cancer Therapy", The New England Journal of Medicine, 354(5): 496-507, Feb. 2, 2006.
Kagawa et al. "Advanced Exercise Control Using Miniature ECG and 3D Acceleration Sensors", D&D Forum on Telemedicine Systems: Issues, design, Development and Standardization at Globecom 2008, New Orleans, Louisiana, USA, 23 P., Dec. 2, 2008.
Katzeff et al. "Exercise Stress Testing and An Electromechanical S Wace of the Electrocardiogram", South African Medical Journal, 49(27): 1088-1090, Jun. 28, 1975.
Kerckhoffs et al. "Homogeneity of Cardiac Contraction Despite Physiological Asynchrony of Depolarization: A Model Study", Annals of Biomedical Engineering, 31: 536-547, 2003.
Kramer et al. "Dielectric Measurement of Cerebral Water Content Using A Network Analyzer", Neurological Research, 14: 255-258, Jun. 1992.
Lee et al. "Noninvasive Tests in Patients With Stable Coronary Artery Disease", The New England Journal of Medicine, 344(24): 1840-1845, Jun. 14, 2001.
Li et al. "An Overview of Ultra-Wideband Microwave Imaging Via Space-Time Beamforming for Early-Stage Breast-Cancer Detection", IEEE Antennas and Propagation Magazine, 47(1): 19-34, Feb. 2005.
McClelland et al. "A Continuous 40 Motion Model from Multiple Respiratory Cycles for Use in Lung Radiotherapy", Medical Physics, 33(9): 3348-3358, Sep. 2006.
Meaney et al. "Microwave Imaging for Neoadjuvant Chemotherapy Monitoring", First European Conference on Antennas and Propagation, EuCAP 2006, Nice, France, Nov. 6-10, 2006, p. 1-4, Nov. 2006.
Meaney et al. "Near-Field Microwave Imaging of Biologically-Based Materials Using A Monopole Transceiver System", IEEE Transactions on Microwave Theory and Techniques, 46(1): 31-45, Jan. 1998.
Nopp et al. "Dielectric Properties of Lung Tissue as A Function of Air Content", Physics in Medicine and Biology, 38(6): 699-716, Jun. 1993.

Panetta "A Mathematical Model of Periodically Pulsed Chemotherapy: Tumor Recurrence and Metastasis in A Competitive Environment", Bulletin of Mathematical Biology, 58(3): 425-447, 1996.
Park et al. "An Ultra-Wearable, Wireless, Low Power ECG Monitoring System", Proceedings of the IEEE Biomedical Circuits and Systems Conference, BioCAS 2006, London, UK, p. 241-244, Nov. 29-Dec. 1, 2006.
Pedersen et al "An Investigation of the Use of Microwave Radiation for Pulmonary Diagnostics", IEEE Transactions on Biomedical Engineering, 23(5): 410-412, Sep. 1976.
Pierard et al. "Stress Testing in Valve Disease", Heart 93:766-772, 2007.
Schantz "Introduction To Ultra-Wideband Antennas", IEEE Conference, On Ultra-Wideband Systems and Technologies, in Brownsboro, AL, USA, On Nov. 16-19, 2003, p. 1-9, 2003.
Schiller "Noninvasive Monitoring of Tumors", The New England Journal of Medicine, 359(4): 418-420, Jul. 24, 2008.
Semenov et al. "Dielectrical Spectroscopy of Canine Myocardium During Acute Ischemia and Hypoxia at Frequency Spectrum From 100 kHz to 6 GHz", IEEE Transactions on Medical Imaging, XP011076314, 21(6): 703-707, Jun. 2002.
Semenov et al. "Three-Dimensional Microwave Tomography: Initial Experimental Imaging of Animals", IEEE Transactions on Biomedical Engineering, XP011007196, 49(1): 55-63, Jan. 2002. Abstract, p. 56, col. 1, Lines 6, 7.
Shea et al. "Contrast-Enhanced Microwave Imaging of Breast Tumors: A Computational Study Using 3D Realistic Numerical Phantoms", Inverse Problems, 26: 1-22, 2010.
Smiseth et al. "Regional Left Ventricular Electric and Mechanical Activation and Relaxation", JACC, Journal of the American College of Cardiology, 47(1): 173-174, Jan. 3, 2006.
Thornton "Optimization of Protocols for Computed Tomography Coronary Angiography", Supplement to Applied Radiology, p. 54-62, Jun. 2002.
Wikipedia "Electronic Packaging", Retrieved from wikipedia.org, 4 Pages, Published Online on Dec. 2006.
Winters et al. "Estimation of the Frequency-Dependent Average Dielectric Properties of Breast Tissue Using A Time-Domain Inverse Scattering Technique" IEEE Transactions on Antennas and Propagation, 54(11): 3517-3528, Nov. 2006.
Winters et al. "Three-Dimensional Microwave Breast Imaging: Dispersive Dielectric Properties Estimation Using Patient-Specific Basis Functions", IEEE Transactions on Medical Imaging, 28(7): 969-981, Jul. 2007.
Yamokoski et al "OptiVol® Fluid Status Monitoring With An Implantable Cardiac Device: A Heart Failure Management System.", 4:(6) 775-780 (doi:10.1586/17434440.4.6.775), Nov. 2007.
Zhou et al. "On the Resolution of UWB Microwave Imaging of Tumors in Random Breast Tissue", IEEE International Symposium of the Antennas and Propagation Society, Jul. 3-8, 2005, 3A: 831-834, Jul. 2005.
Zito et al "Wearable System-On-A-Chip Pulse Radar Sensors For The Health Care: System Overview", 21st Conference on Advanced Information Networking and Applications Workshop (AINAW'07), University of Pisa, Italy—2007, IEEE.
Zlochiver et al "A Portable Bio-Impedance System for Monitoring Lung Resistivity", Medical Engineering & Physics, 29(1): 93-100, 2007.
Notice of Allowance Dated Aug. 16, 2022 From the US Patent and Trademark Office Re. U.S. Appl. No. 16/888,921. (10 Pages).
Notice of Allowance Dated Sep. 29, 2022 from US Patent and Trademark Office Re. U.S. Appl. No. 16/792,357. (12 pages).
Official Action Dated Jun. 8, 2023 from the US Patent and Trademark Office Re. U.S. Appl. No. 18/102,791. (28 pages).
Notice of Allowance Dated Nov. 29, 2023 from the US Patent and Trademark Office Re. U.S. Appl. No. 18/102,791. (28 pages).

\* cited by examiner

METHOD, SYSTEM AND APPARATUS FOR USING ELECTROMAGNETIC RADIATION FOR MONITORING A TISSUE OF A USER

RELATED APPLICATIONS

This application is a continuation of U.S. patent application Ser. No. 13/922,299 filed on Jun. 20, 2013, which is a continuation of U.S. patent application Ser. No. 12/676,385 filed on Jul. 1, 2010, which is a National Phase of PCT Patent Application No. PCT/IL2008/001198 having International Filing Date of Sep. 4, 2008, which claims the benefit of priority from U.S. Provisional Patent Application Nos. 60/969,966, 60/969,965 and 60/60/969,963 all of which were filed on Sep. 5, 2007.

PCT Patent Application No. PCT/IL2008/001198 was also co-filed with PCT Patent Application No. PCT/IL2008/001199 on Sep. 4, 2008.

The contents of the above applications are all incorporated herein by reference.

FIELD AND BACKGROUND OF THE INVENTION

The present invention, in some embodiments thereof, relates to monitoring and, more particularly, but not exclusively, to using EM radiation for monitoring changes of an internal biological tissue.

Medical instruments in which an echo of a pulse of EM radiation is used to detect and locate structures in the human body are known, see YOUNG, J. D et. al. Examination of video pulse radar systems as potential biological exploratory tools in LARSEN, L. E., and JACOBI, J. H. (Eds.): 'Medical applications of microwave imaging' (IEEE Press, New York, 1986), pp. 82-105, which is incorporated herein by reference. Such medical instruments includes microwave imaging devices, which may be referred to as tissue sensing adaptive radar (TSAR) or Imaging and other medical devices for detecting and possibly imaging internal biological tissues. The use of electromagnetic waves eliminates the need to expose the tissues to ionizing radiation, as performed during X-ray imaging, and to obtain relatively large tissue contrasts according to their water content.

One of the most common antennas which are used for such medical instruments is the well-known biconic bow-tie antenna that maintains its port impedance and radiation pattern act in frequencies between certain limits where the low frequency is dictated by the size of the length of the cones and the upper limit by the port capacitance and feeding construction, see Antenna Theory, C. A. Balanis, 2 ed. John Willey, 1997 which is incorporated herein by reference. Such antennas usually suffer from a poor performance at relative low frequencies, where body electromagnetic penetration is better, and a planar construction that may be damaged due to electro-static discharges (ESD).

Such antennas have been used for detecting and imaging various pathologies, such as breast cancer. For example, U.S. Pat. No. 6,061,589 issued on May 20, 2000 describes a microwave antenna for use in a system for detecting an incipient tumor in living tissue such as that of a human breast in accordance with differences in relative dielectric characteristics. In the system a generator produces a non-ionizing electromagnetic input wave of preselected frequency, usually exceeding three gigahertz, and that input wave is used to irradiate a discrete volume in the living tissue with a non-ionizing electromagnetic wave. The illumination location is shifted in a predetermined scanning pattern. Scattered signal returns from the living tissue are collected and processed to segregate skin tissue scatter and to develop a segregated backscatter or return wave signal; that segregated signal, in turn, is employed to detect any anomaly indicative of the presence of a tumor or other abnormality in the scanned living tissue. The present invention is directed to a composite Maltese Cross or bow-tie antenna construction employed to irradiate the living tissue and to collect backscatter or other scatter returns.

In another example, U.S. Pat. No. 6,919,838 published on Jul. 19, 2005, describes a scanner or imager that employs a plurality of microwave transmitters that emit a multiplicity of pulses, which are received by a plurality of receivers. An object or person positioned between the transmitters and receivers can be scanned and subsequently imaged in extreme detail, due to the broad spectral content of the pulses. The scanner can be constructed as a stationary or portable device.

SUMMARY OF THE INVENTION

According to an aspect of some embodiments of the present invention there is provided a wearable monitoring apparatus for monitoring at least one biological parameter of an internal tissue of an ambulatory user. The wearable monitoring apparatus comprises at least one transducer configured for delivering electromagnetic (EM) radiation to the internal tissue and intercepting at least one reflection of the EM radiation therefrom in a plurality of transmission sessions during a period of at least 24 hours, a processing unit configured for analyzing the at least one reflection and identifying a change in the at least one biological parameter accordingly, a reporting unit configured for generating a report according to the change, and a housing for containing the at least one transducer, the reporting unit, and the processing unit, the housing being configured for being disposed on the body of the ambulatory user.

Optionally, the processing unit comprises a communication module for communicating with a remote processing unit thereby allowing performing of at least one of the analyzing and the identifying by the remote processing unit.

Optionally, the processing unit is configured for identifying the change by detecting at least one of a trend, a biological process, and a pattern according to the at least one reflection of the plurality of transmission sessions.

Optionally, the processing unit is configured for evaluating a change in a dielectric related property of the internal tissue in at least one of the plurality of transmission sessions and performing the identification according to the dielectric related property.

Optionally, the plurality of transmission sessions are performed in an adaptive rate.

More optionally, the adaptive rate is determined according to a clinical state of the user, the processing unit being configured for calculating the clinical state according to at least one output of a biological sensor and the at least one reflection.

Optionally, the wearable monitoring apparatus further comprises a posture detection unit configured detecting a posture of the user, the adaptive rate being determined according to the posture.

Optionally, the reporting unit configured for generating the report in real time.

Optionally, the reporting unit is configured for presenting the report to the ambulatory user.

Optionally, the change is indicative of a fluid content change in the internal tissue during the period.

Optionally, the change is indicative of a member of a group consisting of: a trauma a degenerative process, atelectasis, a post-operative atelectasis, an acute respiratory deficiency syndrome (ARDS), an infectious cause, an inhaled toxins, a circulating exogenous toxins, a vasoactive substance, a disseminated intravascular coagulopathy (DIC), a burn, an emphysema, a immunologic processes reaction, a uremia, a post drowning lung water level, a pulmonary venous thrombosis, a stenosis, a veno-occlusive disease, a hypoalbuminemia, a lymphatic insufficiency, a high altitude pulmonary edema (HAPE), a neurogenic pulmonary edema, a drug overdose, a pulmonary embolism, an eclampsia, a postcardioversion, a postanesthetic, a postextubation, and a post-cardiopulmonary bypass an inflammation progress of ARDS users, postoperative atelectasis.

Optionally, the housing is configured for being disposed on the body of the ambulatory user during a physical exertion thereof, the change being indicative of a fluid content change resulting from the physical exertion.

Optionally, the wearable monitoring apparatus further comprises a repository configured for storing information pertaining to the user, the processing unit being configured for performing the analyzing with respect to the information, wherein the information comprises at least one of physiological, anatomical, and clinical data related to the user.

Optionally, the wearable monitoring apparatus further comprises a non EM radiation sensor configured for evaluating an indicator of the physical condition of the user, the processing unit being configured for performing the analyzing with respect to the evaluated indicator.

More optionally, the processing unit is configured for identifying the change by a combination of the indicator and the at least one reflection of the plurality of transmission sessions.

More optionally, the non EM radiation sensor is a member of a group consisting of electromyogram (EMG), an ultrasound transducer, a blood pressure sensor, an optical blood saturation detector, a pulse oximeter, electrocardiogram (ECG), tiltmeter and accelerometer an activity sensor, and a coagulometer.

Optionally, the wearable monitoring apparatus further comprises a biological sensor configured detecting a pattern of a vital physiological activity of the user, the processing unit being configured for performing the analyzing with respect to the pattern.

More optionally, the pattern is a member of a group consisting of: a heart beat rate, breathing cycle, systole diastole cardiac cycle, and a blood cycle effect on the internal tissue.

Optionally, the processing unit is configured for detecting a pattern of a vital physiological activity of the user by analyzing the at least one reflection, the processing unit being configured for performing the analyzing with respect to the pattern.

More optionally, the pattern is a member of a group consisting of: a systole diastole cardiac cycle and a breathing cycle.

Optionally, the processing unit is configured for detecting a vital physiological activity of the user by analyzing the at least one reflection, the processing unit being configured for performing the identifying with respect to the vital physiological activity.

Optionally, the wearable monitoring apparatus further comprises a posture detection unit configured detecting a posture of the user, the processing unit being configured for analyzing the at least one reflection with respect to the posture.

Optionally, the change is indicative of a change in the concentration of a solute in the internal tissue.

More optionally, the solute is a member of a group consisting of a salt, glucose, and or inflammatory indicative fluid.

Optionally, the reporting unit is configured for transmitting the report to a management center.

Optionally, the EM radiation comprises a narrowband signal of less than 50 Mega Hertz (MHz) bandwidth and a pulse signal of at least 0.5 gigahertz (GHz) bandwidth.

Optionally, the EM radiation is transmitted in a swept frequency mode.

Optionally, the EM radiation is transmitted in a plurality of frequencies.

Optionally, the wearable monitoring apparatus further comprises a placement unit for providing a position of the at least one transducer in relation to a reference internal tissue of the user, the delivering being performed with respect to the position.

Optionally, the wearable monitoring apparatus further comprises a placement unit configured for receiving a positioning data indicative of a historical position of at least one of a similar wearable monitoring apparatus and the wearable monitoring apparatus in relation to at least one reference internal tissue, the placement unit being configured for using the historical position as a reference for positioning the wearable monitoring apparatus.

Optionally, the at least one transducer comprises a planar wide band antenna.

Optionally, the at least one transducer is positioned in proximity to the skin of the ambulatory user.

Optionally, the housing is configured to be integrated into a garment.

Optionally, the reporting unit is configured for forwarding the report to a dosage control unit, the dosage control unit being configured for at least one of dispensing of a medication according to the report and presenting a dosage recommendation according to the report.

More optionally, the housing containing the dosage control unit.

More optionally, the dispensing is related to an oncology treatment.

Optionally, the processing unit is configured for identifying the change using a tissue model adapted to the internal tissue.

Optionally, the at least one transducer comprises a plurality of transducers configured for delivering EM radiation to the internal tissue and intercepting the at least one reflection therefrom.

More optionally, the plurality of transducers comprises at least one transmitter configured for performing the delivering and at least one receiver configured for performing the intercepting.

More optionally, the at least one transducer being configured for intercepting the at least one reflection from a plurality of sub-areas of the internal tissue for improving the resolution of the at least one reflection.

More optionally, the processing unit is configured for reducing at least one of a noise, a disturbance, a posture movement effect and/or an interference intercepted by the at least one first transducer by comparing portions of the at least one reflection from the first and second sub-areas.

According to an aspect of some embodiments of the present invention there is provided a system for monitoring at least one biological parameter of an internal tissue of a plurality of ambulatory users. The system comprises a plurality of wearable devices, each configured for being disposed on the body of one of the plurality of ambulatory users and for identifying a change in the at least one biological parameter according to at least one reflection of electromagnetic (EM) radiation from an internal tissue of a respective of the ambulatory users and a user management unit configured for receiving the identified change from a respective the wearable device and generating a report accordingly.

Optionally, the user management unit is configured for alerting a caretaker by forwarding the report to a remote client terminal associated with the caretaker.

Optionally, the remote client terminal is a member of a group consisting of a cellular phone, a computer, a medical data center, medical data system, and a medical database.

Optionally, the user management unit is configured for updating at least one of the plurality of wearable devices with medical data related to a respective of the plurality of ambulatory users.

Optionally, the user management unit is configured for prioritizing a treatment to at least some of the plurality of ambulatory users according to respective the identified change.

Optionally, the user management unit is configured for receiving a technical status indication from each the wearable device.

Optionally, the user management unit is configured for forwarding at least one of the report and the identified change to allow updating of a medical data system.

According to an aspect of some embodiments of the present invention there is provided a wearable monitoring apparatus for identifying a posture of a user. The wearable monitoring apparatus comprises at least one transducer configured for delivering electromagnetic (EM) radiation to an internal tissue and intercepting a reflection of the EM radiation therefrom, a processing unit configured for analyzing the reflection and identifying a posture of the user accordingly, and an output unit configured for generating an indication of the posture.

Optionally the apparatus further comprises a housing for containing the at least one transducer, the processing unit and the output unit, the housing being configured for being disposed on the body of the user.

More optionally, the housing comprises a biological probe.

Optionally, the output unit is configured for presenting at least one movement instruction to execute a predefined posture according to the posture.

Optionally, the apparatus further comprises a sensor for detecting a biological parameter, the processing unit configured for performing the identifying with respect to the biological parameter.

According to an aspect of some embodiments of the present invention there is provided a wearable monitoring apparatus for detecting a posture of a user. The wearable monitoring apparatus comprises at least one transducer configured for delivering electromagnetic (EM) radiation to an internal tissue and intercepting a reflection of the EM radiation therefrom, a processing unit configured for analyzing the reflection and identifying a positioning of the internal tissue in relation to the EM radiation accordingly, and an output unit configured for generating an indication of the positioning.

According to an aspect of some embodiments of the present invention there is provided a method for detecting a body posture. The method comprises delivering electromagnetic (EM) radiation to an internal tissue of a user, intercepting a reflection of the EM radiation therefrom, and identifying a change in the posture of the user according to the reflection.

Optionally, the EM radiation comprises a narrowband signal of less than 50 Mega Hertz (MHz) bandwidth and a pulse signal of at least 0.5 gigahertz (GHz) bandwidth.

According to an aspect of some embodiments of the present invention there is provided an apparatus for detecting a misplacement of a biological probe in relation to an internal tissue of a user. The apparatus comprises a repository configured for storing at least one reference value indicative of an at least one exemplary reflection of electromagnetic (EM) radiation delivered to an internal tissue of the user, at least one transducer configured for delivering, the EM radiation to the internal tissue and intercepting at least one actual reflection of the EM radiation therefrom, and a processing unit configured for identifying the misplacement by comparing between the at least one reference value and an actual value calculated according to the intercepting at least one actual reflection.

Optionally, the EM radiation comprises a narrowband signal of less than 50 Mega Hertz (MHz) bandwidth and a pulse signal of at least 0.5 gigahertz (GHz) bandwidth.

Optionally, the at least one reference value is a range of values.

Optionally, the apparatus further comprises an output unit configured for forwarding an indication pertaining to the misplacement to a remote system via a communication network.

Optionally, the apparatus further comprises a guiding unit configured for presenting at least one repositioning instruction directing at least one of the user and a caretaker to reposition the biological probe according to the identified misplacement.

Optionally, the apparatus further comprises a mechanical adjustment unit for automatically changing the position of the biological probe according to the identified misplacement.

Optionally, the apparatus further comprises a communication interface configured for notifying a management node about the misplacement.

More optionally, the management node is configured for changing a billing data pertaining to user according to the indication.

Optionally, the biological probe is a wearable element.

According to an aspect of some embodiments of the present invention there is provided a method configured for detecting a misplacement of a biological probe in relation to an internal tissue of a user. The method comprises providing at least one reference value indicative of an at least one exemplary reflection of electromagnetic (EM) radiation delivered to an internal tissue of a user wearing the biological probe, delivering the electromagnetic (EM) radiation to the internal tissue, intercepting a at least one actual reflection of the EM radiation therefrom, and identifying the misplacement by comparing between the a actual value calculated according at least one actual reflection and the at least one reference value.

Optionally, the method further comprises presenting a set of instructions for instructing the placement of the biological probe according to the misplacement.

Optionally, the EM radiation comprises a narrowband signal of less than 50 Mega Hertz (MHz) bandwidth and a pulse signal of at least 0.5 gigahertz (GHz) bandwidth.

Optionally, the method further comprises receiving positioning data related to a previous positioning of the biological probe, the misplacement identified in relation to the positioning data.

According to an aspect of some embodiments of the present invention there is provided a wideband antenna. The wideband antenna comprises a printed metallic field transducer for transmitting EM radiation and an arrangement of at least one lumped absorbing element. The arrangement having a minimal absorption area absorbing at least 75% of the energy absorbed by the arrangement. The a first distance is the smallest distance between a geometric center of the printed metallic field transducer and a perimeter encircling a transmission area of the printed metallic field transducer required for transmitting 50% of the energy of the EM radiation in the lowest end of a used frequency band with respect to infinite size transducer. The distance of each point within the minimal absorption area from the geometric center is at least the first distance.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a monitored user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
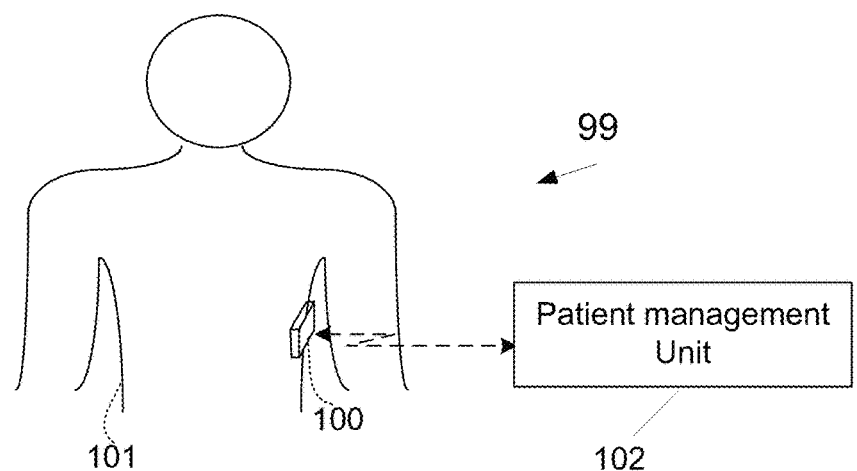
FIG. 1 is a schematic illustration of a wearable monitoring apparatus that is attached to the thorax of a user 101 and optionally connected to a user management unit, according to some embodiments of the present invention.

The present invention, in some embodiments thereof, relates to monitoring and, more particularly, but not exclusively, to using EM radiation for monitoring changes of an internal biological tissue.

According to some embodiments of the present invention, there is provided a method and a wearable monitoring apparatus for monitoring one or more biological parameters of an internal tissue of an ambulatory user. The apparatus is based on one or more transducers for delivering electromagnetic (EM) radiation to the internal tissue and intercepting a reflection of the EM radiation therefrom in a plurality of transmission sessions, which may be continuous or intermittent. The apparatus comprises a processing unit that is used for evaluating the change of fluid content of the internal tissue along the monitoring period according to the reflections captured during the sessions and identifying a change in the biological parameters accordingly. The apparatus further comprises a reporting unit for generating a report according to the change. The report may be forwarded to an MMI unit on the wearable monitoring apparatus and/or to a remote management node, such as a medical center and/or a patient management unit.

The apparatus comprises a housing, which is optionally designed to be attached to the body of the patient without substantially changing her general body contour, for containing the transducers, the reporting unit, and the processing unit. The housing is disposed on the body of the ambulatory user that is not confined to a certain location in which monitoring is conducted. Optionally, in order to reduce the air-skin interface and/or positioning change, the transducers are positioned concomitantly to the body of the ambulatory user.

In some embodiments of the present invention, there is provided a system for monitoring biological parameters of an internal tissue of a plurality of ambulatory and/or hospitalized users. The system is based on a plurality of wearable devices, each designed for being disposed on the body of one of the plurality of ambulatory and/or hospitalized users and for evaluating a change in a dielectric related property of an internal tissue thereof. The system further comprises a user management unit configured for receiving the evaluated changes from the wearable device and generating an alert accordingly, for example by displaying a respective indication to a caretaker. Such a system may be used to monitor biological parameters of a plurality of ambulatory and/or hospitalized users, to gather statistics on these biological parameters, to prioritize treatment to the plurality of users and the like.

According to some embodiments of the present invention there is provided a method and an apparatus for detecting misplacement, placement, and or disengagement of a biological probe, such as the wearable monitoring apparatus which is outlined above, in relation to an internal tissue of a user. The apparatus comprises a memory element, which may be referred to herein as a repository, for storing reference values each indicative of an exemplary reflection of EM radiation delivered to an internal tissue of the user from the biological probe and one or more transducers for delivering, from the biological probe, the EM radiation to the internal tissue and intercepting an actual reflection of the EM radiation therefrom. The apparatus further comprises a processing unit for identifying the misplacement by comparing between the reference values and the actual reflection. Such an apparatus may be used for verifying patient compliance, alerting a user when the biological probe is misplaced, and/or for guiding a placing and/or a replacing of the medical biological probe.

According to some embodiments of the present invention there is provided a wearable monitoring apparatus for detecting a posture of a user. The wearable monitoring apparatus may be integrated with the above mentioned apparatuses or with any medical biological probe which is used for monitoring a biological parameter of a patient and may be affected by the posture thereof. The apparatus comprises one or more transducers for delivering EM radiation to an internal tissue and intercepting a reflection of the EM radiation therefrom and a processing unit for evaluating a dielectric related property of the internal tissue by analyzing the reflection and identifying a posture of the user and/or a change of the posture of according to the intercepted reflections. The apparatus further comprises an output unit configured for generating an indication of the posture and the change. Such an indication may be used for registration of related biological parameters, generating an alert and/or a report which is related to the physical condition of the user.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a schematic illustration of a wearable monitoring apparatus 100 that is attached to the body of a user, optionally to the thorax, as shown at 101. The wearable monitoring apparatus 100 is optionally connected to a user management unit 102, optionally in a bidirectional wireless connection, according to some embodiments of the present invention.

It should be noted that the wearable monitoring apparatus 100 and/or the user management unit 102 may interface with and/or integrated to different systems of various medical centers, such as hospitals, caretaker clinics, long term care facilities, nursing homes, and home care settings. As used herein a caretaker means a physician, a nurse, a family member, an affiliate, a medical center staff member, a call center any entity which is in charged and/or should have access to the medical condition of the monitored user and/or a team of one or more of these caretakers.

The wearable monitoring apparatus 100 is designed for monitoring one or more clinical parameters of an internal tissue and/or an organ by detecting changes in the fluid content and/or composition, for example according to changes in the fluid content thereof, for example according to dielectric related properties that reflect changes in the amount of fluids, such as water, blood, and/or inflammation fluids in the monitored internal tissue and/or organ, for example in the pulmonary tissues of the user 101 and/or in the area between the pericardium and the heart and/or in the area between the visceral and parietal pleura. As used herein a dielectric related property of a specific volume means the magnetic permeability and electric permittivity of the composite material within a specific volume. Such a dielectric related property may be affected by a presence of fluid, a concentration of substances, such as salts, glucose, in the fluid in the internal tissue and/or organ, the ratio of fibrotic tissue, and a concentration of inflammatory substance in the fluid in the internal tissue and/or organ.

In one example of the present invention, the wearable monitoring apparatus 100 is attached to the skull of a user and used for monitoring a build up of intra-cranial pressure which may be a consequence of a head injury. In another of example of the present invention, the wearable monitoring apparatus 100 may be attached to the abdomen for monitoring abdominal bleeding, which may be a consequence of abdominal surgery. In another example, the wearable monitoring apparatus 100 is positioned on the lower abdomen for monitoring prostate related treatments, such as irradiation and/or medication for carcinoma.

Optionally, the wearable monitoring apparatus 100 is designed to be attached to the thorax of a user 101, optionally as described below. The wearable monitoring apparatus 100 may communicate, optionally wirelessly, with a user management unit 102, which may be connected to the hospital IT unit, an emergency center and/or to a disease management center.

Optionally, the wearable monitoring apparatus 100 comprises a thin housing, optionally curved for allowing the attaching thereof to the body of the user 101 without substantially changing her general body contour, for example as described below. Optionally, the wearable monitoring apparatus 100 and/or the housing thereof is designed to be flexible in a manner that allows the attaching thereof to people with different contours and/or encirclement, Optionally, the wearable monitoring apparatus 100 and/or the housing thereof is provided in various sizes.

The attaching of the wearable monitoring apparatus 100 to the thorax of the user allows the user to wear it below a common blouse or a shirt. Optionally, the thin housing, which is designed to contain all the integral parts of the monitoring apparatus 400, including a processing unit and one or more EM transducers which are designed to implement monitoring methods, for example as described in co filed Patent application by Dan RAPPAPORT, Nadav MIZRAHI, Shlomi BERGIDA, Amir SAROKA, Amir RONEN, and Ilan KOCHBA titled method and system for monitoring thoracic fluids which the content thereof is incorporated herein by reference. For brevity, this application may be referred to herein as the co filed Patent Application. Optionally, the wearable monitoring apparatus 100 is connected to a battery, optionally rechargeable.

Optionally, the wearable monitoring apparatus 100 is attached to the body of the user 101. Optionally, the wearable monitoring apparatus 100 includes a replaceable body coupler that increases the contact between the wearable monitoring apparatus 100 and the user's body and optionally reduces the skin irritation which could have been caused by the wearable monitoring apparatus 100.

In some embodiments of the present invention, the wearable monitoring apparatus 100 is designed to continuously track, in a plurality of transmission sessions, the fluid content n an internal tissue of the user 101, such as the pulmonary fluid content user. As further described in the co filed Patent Application, the wearable monitoring apparatus 100 may be used for performing such monitoring for hospitalized and non hospitalized users during a monitoring period which is longer than 1, 2, 4, 8, 12, 16, 20 and 24 hours, days, weeks, mouths, and/or years. Such monitoring includes capturing reflections while the user is ambulatory. As used herein, ambulatory means a user which is not confined to a certain location where monitoring is conducted. For example, ambulatory users may be monitored for periods which are longer than one hour, without being confined to a certain area and immobilized users may be monitored for long periods, for example for periods of 24 hours or more, without having to lay in a designated hospitalization room that is equipped with a stationary monitoring device.

In some embodiments of the present invention, the wearable monitoring apparatus 100 is responsible for the continuous and/or repetitive monitoring the fluid content, and optionally additional clinically related parameters, in order to indicate a biological and/or clinical condition of the user and/or to alert or notify the user 101 and/or the user management unit 102 about a biological process, such as a wellness indicative process, a pathological process and/or a cause of a disease that is detected according to the detection of an dielectric related properties As used herein, pathological processes, pathological conditions, and causes of diseases mean degenerative processes, trauma, atelectasis, post-operative atelectasis, acute respiratory deficiency syndrome (ARDS), an infectious causes, an inhaled toxins, a circulating exogenous toxins, a vasoactive substances, a disseminated intravascular coagulopathy (DIC), a immunologic processes reactions, a uremia, a post drowning lung water level, a pulmonary venous thrombosis, a stenosis, burns, a veno-occlusive disease, a hypoalbuminemia, an emphysema, a lymphatic insufficiency, a high altitude pulmonary edema (HAPE), a neurogenic pulmonary edema, a drug overdose, a pulmonary embolism, an eclampsia, a postcardioversion, a postanesthetic, a postextubation, a postcardiopulmonary bypass an inflammation progress of ARDS users, postoperative atelectasis and/or any other pathological process and/or cause of a disease with abnormal fluid content in an internal body area as a symptom or epiphenomenon. As used herein a biological process means a process occurring in living organism as an outcome of a normal and/or abnormal physical action of the user, such as an athletic activity, for example hiking. The wearable monitoring apparatus 100 may use repetitive, continuous or intermittent measurements for monitoring of abnormal biological processes and/or changes in the routine of the user, for example monitoring the effect of a certain physical exertion, a diet and/or an altitude change on the monitored user. Such monitoring may allow alerting the user about fat to water ratio decrease, prospective dehydration and/or altitude sickness. Optionally, the wearable monitoring apparatus 100 is configured for continuously monitoring changes in the dielectric related properties of one or more internal tissues. The reflection of the EM radiation, which is intercepted by the EM transducers wearable monitoring apparatus 100 are analyzed to allow tracking and/or detecting of anatomical, physiological, and/or pathophysiological parameters. Such an analysis, which may be performed locally on the wearable monitoring apparatus 100 and/or using a central server, for example as depicted at 102 of FIG. 2 facilitate generating a clinical status report and/or alert, for example as described below.

Optionally, the analysis allows gathering data, which is based on the intercepted reflections, which reflects a trend, a pathological pattern, and/or one or more deductive or observational measurements that reflect a change in the fluid content of an internal tissue. For brevity, the outcome of such an analysis may be referred to herein as a change. In use, as further described below, such an analysis allows the communication interface to send a report that is indicative of this change and the MMI 207 to present the change and/or an alert which is based thereon. For brevity, a communication interface and/or unit, as shown at 208, which allows forwarding data, such as the report, to third parties, such as the patient management unit 102 and the interrogator 152, and a presentation unit, such as the MMI 207, may be referred to herein as reporting unit.

The wearable monitoring apparatus 100 may function as an independent monitoring device, as a sensing unit of a monitoring system, and/or as a monitoring device that communicates with a central computing unit, such as the user management unit 102, during a period which is longer than 1, 2, 4, 8, 12, 16, 20 and 24 hours, days, weeks, mouths, and/or years, in an intermittent or continuous measurement manner. In such an embodiment, the monitoring device may be used for gathering, and optionally analyzing, data, such as dielectric related properties of the internal tissues, such as the pulmonary tissues, and transferring the gathered and/or analyzed data to the user management unit 102 for producing a detailed report, a notification, and/or an alert.

As used herein, an analysis may include processing any digitized signal of any of sensors, such as the front end sensors which are described below, for alerting, reporting, and/or allowing any other functionality of the user management unit 102 and/or the wearable monitoring apparatus 100, for example for determining one or more clinical parameters, such as physiological, pathophysiological, and anatomical parameters, determining clinical status of the user, such as a overall health score, determining a specific disease status, determining trends of change, determining a probability of change, and determining one or more alert events.

Alternatively or additionally, the wearable monitoring apparatus 100 is designed for locally analyzing the dielectric related properties of internal tissues, such as the pulmonary tissues, in a manner that allows the generation of a real time alert, for example as described in the co filed Patent Application. In this context, the term "real time" means that the time the wearable monitoring apparatus 100 and/or the user management unit 102 takes to output an alert and/or a clinical status is sufficiently short not to introduce any significant delay in time between the analyzing the dielectric related properties of internal tissues and the generation of a real time alert.

In some embodiments of the present invention, the analysis allows calculating a biological parameter, such as a clinical state, of a user based on an integrative index. The biological parameter may be determined based on a combination between the dielectric related properties of an internal tissue, such as the pulmonary tissue, and/or fluid content build up pace and vital signs and/or detected trends of vital signs which are acquired using one or more additional sensors.

Such additional sensors may include sensors such as electrocardiogram (ECG), electromyogram (EMG), an ultrasound transducer, a blood pressure sensor, for example an ultrasonic sensor, a pulse oximeter, activity sensors, for example accelerometers and tiltmeters, microphone, capnometer, a coagulometer and any sensor configured for gathering data related to the physical condition of the monitored user. As used herein, a physical condition means data related to the physical activity, vital signs, biological parameters, and/or any other medical and/or biological information which indicative of the user wellness and/or fitness of the monitored user.

The biological parameter, which may be referred to any one or more values of biological indicators which reflect a status of a human and/or an organ and/or a tissue thereof, may be determined based on a combination between the dielectric related properties of the monitored internal tissue and and/or organ, which optionally are indicative of a fluid content and/or a fluid content build up pace and user related medical data, such as medical history, a diagnosis of the treating physicians, pathology information and thresholds.

Optionally, biological parameter may be determined based on a combination between the dielectric related properties and additional data that is acquired using the EM transducers, such as breathing rate and/or depth and heart rate. Optionally, biological parameter may be determined based on a combination between the dielectric related properties user related data from external sources and/or sensors. Such data may include real time clock reading, medical and/or physiological data which is updated and/or entered by a caretaker, statistical data provided by the user management unit 102, and/or manually inputted parameters.

The data which is acquired from the EM transducers and/or from the additional sensors allows improving the accuracy of the acquired biological, optionally clinical, parameters by detecting and deducing the effect of internal and/or external physiological activities of the monitored user. For clarity, effects of internal physiological activities may include heart beat rate, breathing cycle, and/or blood cycle and effects of external physiological activities may include effects of posture change, sweating, and/or external body heat. For brevity, different positioning of an internal organ and/or tissue in relation to the EM transducers may also be referred to herein as different postures.

The integrative index is optionally scaled and/or color coded to provide intuitive follow-up of the clinical status of the user. The medical sensors may be embedded into the wearable monitoring apparatus 100 and/or communicate therewith via a communication interface. In such an embodiment, the wearable monitoring apparatus 100 may determine a current clinical state of the user according to various vital signs, for example according to known multi-parameters pattern classification algorithms, such as Bayesian based algorithms and neural networks based algorithms.

Optionally, dielectric related properties and/or dielectric related properties dielectric related properties and/or the vital signs trends are calculated from recorded and/or logged dielectric related properties of the user. In such an embodiment, the dielectric related properties of the monitored tissue may be collected during a period which is longer than 1, 2, 4, 8, 12, 16, 20 and 24 hours, days, weeks, mouths, and/or years. In such a manner patterns and/or pace of the accumulation and/or change in one or more dielectric related properties may be detected. For example, as described in the co filed Patent Application, the pathological pulmonary fluid content, which are calculated by the wearable monitoring apparatus, are recorded and used for detecting dielectric related properties, such as an accumulation and/or a presence pace.

As the wearable monitoring apparatus 100 allows monitoring and/or detecting dielectric related properties and/or a change, such as a fluid content change, a pattern of an accumulation and/or a dispersal of fluid, within a specific area of interest, a process, such as parenchyma in the micro level and/or a change of composition in the macro level of a tissue, such as the monitored tissue. Optionally, the monitoring and/or detection is based on gathered data during one or more transmission sessions, from one or more front end sensors, and on the analysis thereof for detecting a change caused by a trend, a pathological pattern, and/or a gradual process. Such an analysis may be based on combination of outputs from a plurality of sensors. In some embodiments of the present application, the gathered data is used for detecting such a change by arranging data in single and/or multiple dimensional model and optionally comparing the model to a reference model and/or baseline that reflect a trend, a pathological pattern, and/or a gradual process. An example for such a model may be a model, such as a 4D model, which reflects changes in a multi dimensional model, such as a 3D model, during a period. The multi dimensional model may reflect dielectric related properties from one or more areas in the monitored tissue, a blood pressure, an activity level, a glucose level, body temperature, body mass, and/or the composition of the fluid content in the one or more areas of the monitored tissue.

Additionally or alternatively, the wearable monitoring apparatus 100 may be used for an early detection of pathological exacerbation, tailored titration of medical treatments and/or monitoring of the user's clinical status. Optionally, the wearable monitoring apparatus 100 may be used for monitoring CHF users for the purpose of detecting the early stages of decompensation states and/or processes and reduced heart functionalities. Such an early detection allows a timely treatment that alleviates the symptoms and may prevent or shorten the hospitalization period of the user and/or reduce morbidity and/or mortality.

Optionally, the wearable monitoring apparatus 100 is used for improving a titration and/or a prognosis process. For example, angio-genesis medication, chemotherapy and/or irradiation treatments may be titrated optimized according to readings of the wearable monitoring apparatus 100. The optimization may be performed by adjusting the type, intensity and repeatability of these treatments. Such monitoring allows reducing the exposure of the user to chemical agents and ionizing radiation by adjusting their amount according to dielectric related properties of the monitored tissue, for example by checking the actual concentration of fluids and/or accumulation patterns. Optionally, the monitoring allows monitoring the concentration of inflammatory fluids in and/or between internal tissues. Optionally, the monitoring allows evaluating the composition of fluids which are accumulated in and/or between internal tissues, for example the concentration of a salt, glucose, an anti inflammatory agent and/or a combination thereof in a certain internal tissue. Such monitoring allows estimating the wellness of the tissues and/or the pathological condition thereof.

Optionally, the wearable monitoring apparatus 100 is used for alerting the user and/or a medical center about one or more predefined and/or known biological patterns. such as pathological patterns of one or more of the following: a degenerative process, acute respiratory distress syndrome (ARDS), congestive heart failure (CHF), an atelectasis, a post-operative atelectasis, a postoperative process, an osculated bronchus, a pulmonary inflammation progress, a pulmonary blood accumulation, acute respiratory deficiency syndrome (ARDS), an infectious causes, an inhaled toxins, a circulating exogenous toxins, a vasoactive substances, a disseminated intravascular coagulopathy (DIC), a immunologic processes reactions, a uremia, a post drowning lung water level, a pulmonary venous thrombosis, a stenosis, a veno-occlusive disease, a hypoalbuminemia, a lymphatic insufficiency, a high altitude pulmonary edema (HAPE), a neurogenic pulmonary edema, a drug overdose, a pulmonary embolism, an eclampsia, a postcardioversion, a postanesthetic, a postextubation, and post-cardiopulmonary bypass. The predefined and/or known biological patterns may include a pattern of a monitored physiological activity, such as a physical exertion and/or a predefined and/or known change that correspond with such a physiological activity. The ability to alert the user and/or a medical center about one or more predefined and/or known biological patterns may be performed by an alerting mechanism which is either implemented on the wearable monitoring apparatus 100, on a remote medical data center and/or on a combination thereof, for example as described below.

Optionally, the wearable monitoring apparatus 100 is used for monitoring ARDS users. In such an embodiment, the wearable monitoring apparatus 100 is used for monitoring inflammation progress along the treatment. Optionally, the wearable monitoring apparatus 100 comprises multiple front end sensors which are used for monitoring, optionally dynamically, the spreading of the inflammation in one or more areas, optionally in response to an antibiotic medication treatment.

Optionally, the wearable monitoring apparatus 100 is used for detecting a progression of post operative atelectasis. Such an early detection may allow the user to prevent exacerbation of the user's condition.

Figure 2:
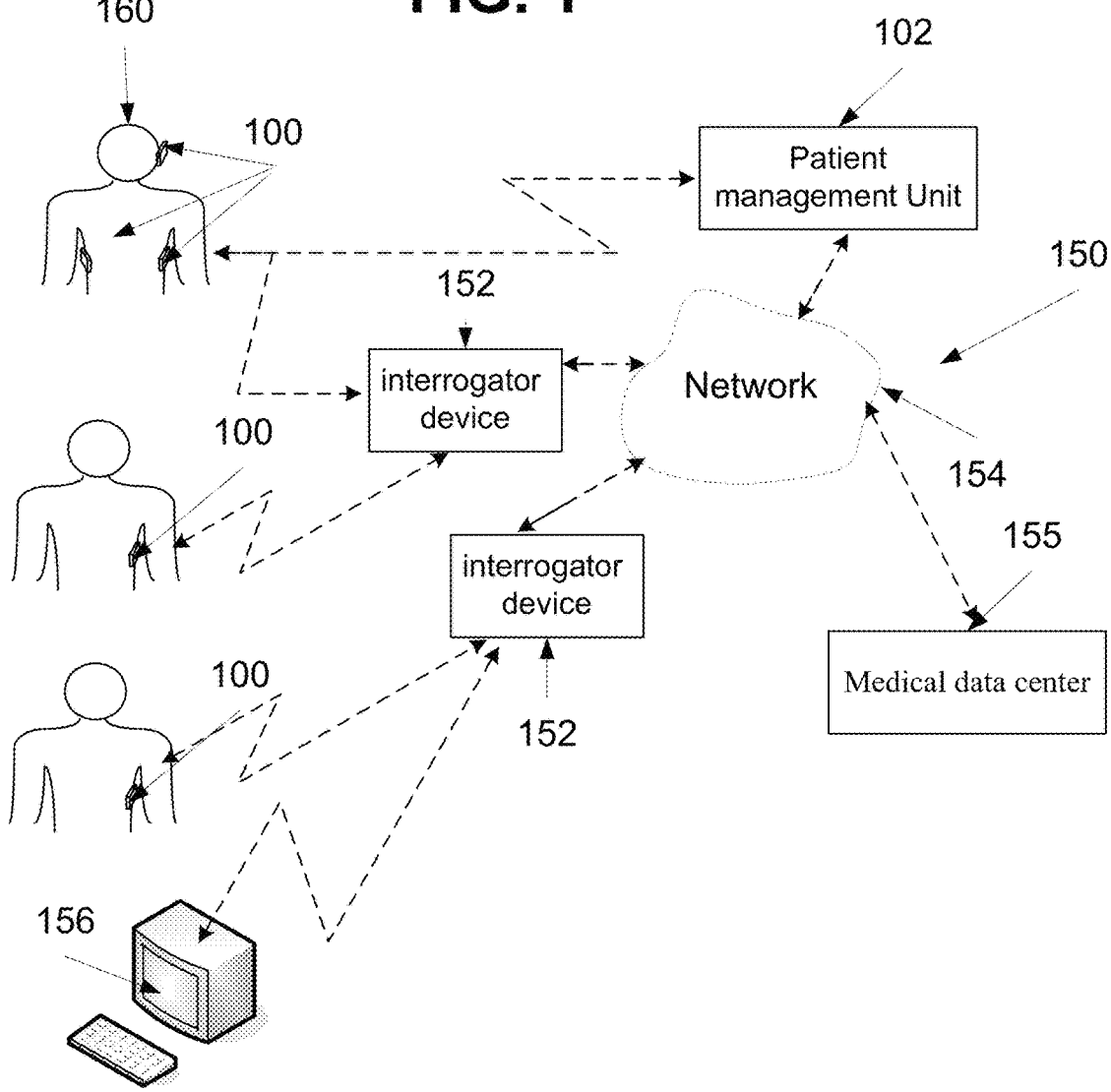
FIG. 2 is a schematic illustration of an exemplary system for managing the monitoring dielectric related properties of internal tissues of one or more users, according to some embodiments of the present invention.

Reference is now made to FIG. 2, which is a schematic illustration of an exemplary system 150 for managing the monitoring of dielectric related properties of internal tissues of one or more users, according to some embodiments of the present invention. The exemplary system 150 comprises one or more wearable monitoring device 100, optionally as outlined above and described below and a user management unit 102, optionally as outlined above and described below. In some embodiments of the present invention, the user management unit 102, which may be referred to herein as a central server, communicates with the one or more wearable monitoring devices 100 via a computer network 154. As further described below, each one of the one or more wearable monitoring devices 100 may be used for analyzing inputs which are received from their front end sensors and to produce one or more alerts and/or reports accordingly. Optionally, the user management unit 102 is designed to receive the inputs which are received from their front end sensors and to analyze and/or generate reports and/or alerts in a similar manner.

As further described below, the wearable monitoring apparatus 100 may be used for gathering data from one or more sensors, such as EM transducers. The gathered data is either analyzed for detecting dielectric related properties and/or dielectric related properties changes in an internal tissue of the user and/or forwarded for analysis by the user management unit 102.

Optionally, the wearable monitoring apparatus 100 forwards, optionally periodically, the gathering data, analyzed or not, to an interrogator device 152. The interrogator device 152 may be used for forwarding the data to the user management unit 102. Optionally, the interrogator device 152 forwards, optionally periodically, instructions, updates, and/or reconfigurations from the user management unit 102 to the wearable monitoring apparatus 100.

Optionally, the user management unit 102 controls and manages, optionally technically, the one or more interrogator devices 152, the one or more wearable monitoring apparatuses 100, and one or more user management unit 102. Optionally, the user management unit 102 monitors the robustness of the system 150 its operations, allows remote configuration via the network 154, to activate and/or deactivate any of the system components. Optionally, the user management unit 102 may collect clinical data from the wearable monitoring apparatuses 100 or other of the components of the system, analyze collected data, manage alerts, maintain and manage a central database containing user clinical data, such as current measurements, historical measurements, alerts, analysis outputs, treatment information, user entered information, component statuses, component performances, component version history data, and system management information. Optionally, the user management unit 102 may facilitate and control access to the information in the database for authorized system operators, users, and/or caretakers, for example via remote client terminals 156 which are connected to the network 154. For example, a user may access records which are related to the outputs of her wearable monitoring apparatus 100 for purposes of getting feedback related to medical condition and/or user compliance. In another example, the user's caretaker and/or an authorized family member may access the respective data for doing the same. Optionally, the user management unit 102 may monitor the technical status and/or operation of the wearable monitoring apparatuses 100. In such manner, the user management unit 102 may alert the user and/or the caretaker about previous, concurrent, and/or prospective malfunctions of the wearable monitoring apparatuses 100 Optionally, the wearable monitoring apparatuses 100 are designed to sent, periodically, continuously, randomly and/or upon the occurrence of one or more predefined events, data, such as technical status report, to the user management unit 102.

Optionally, the user management unit 102 may facilitate prioritization of a medical treatment and/or procedure to users which are managed by the system 150. The user management unit 102 may allow a priority driven management of the users according to the inputs which are received from the wearable monitoring apparatus 100 and/or the analysis that is performed by them, for example according to the fluid content in the pulmonary tissue of the monitored users. In use, the user management unit 102 may display a GUI that includes a list of all users which are monitored by the system 150. The list may be ordered according to current medical risk values which are given to the users. Optionally, the user management unit 102 may be designed to send an email, an instant message, an MMS, an SMS, and/or any other digital content message that includes identifiers of users with a medical risk above a predefined threshold to a designated address.

Optionally, the user management unit 102 monitors the functionality of components of the system 150 and/or the communication among components of the system 150. Optionally, if a failure is detected, a technical alert event is initiated any transmitted to any of the components of the system 150 via technical communication channels, as further described below. For example, one of the wearable monitoring devices 100 may be polled via the aforementioned technical communication channels to ensure its proper previous, current, and/or prospective functionality and/or positioning, for example by querying the placement unit, which is described below. Similarly, other components of the system could be checked for proper functionality. Optionally, each one of the component may implement a local technical monitoring functionality. If a local problem is detected it may relay it to any other component of the system through the aforementioned communication channels. The local technical monitoring functionality may manage the replacement of the wearable monitoring devices 100 and/or the battery thereof.

Optionally, the technical communication channels may allow updating the wearable monitoring devices 100 with new operation modes, software and/or firmware versions, and/or parameters of monitoring algorithms and/or any other functional algorithms, initiating measurements. Optionally, the technical communication channels may allow initiating a transfer of data, deactivate the wearable monitoring devices 100, activate the wearable monitoring devices 100, allowing a remote access to low level memory content, initiating self tests, resetting and the like.

Optionally, the system 150 is connected to central medical units and/or medical data centers 155 which are designed to manage medical data that is related to the monitored users. In such an embodiment, the data that is gathered by the wearable monitoring apparatus 100 and/or the analysis, reports, and/or alerts which are based thereon are collected and/or managed by the central medical units and/or data centers 155, which may be referred to herein as medical data centers 155.

It should be noted that the system's functionality may be implemented using some or all of the above mentioned components and multiple partitioning configurations of the functionalities across the components are possible, for example as described below. Any of these components may be implemented as a separate device with hardware and software; it may also be integrated into existing third party devices and software application. For example, the user interrogator device 152 may be integrated into a standard hospital monitor, a third party tele-health gateway in the user's home, or a smartphone or a PDA. In another example, the patient management unit 102 may be integrated into the IT central station application used in the hospital.

Optionally, the communication between the components of the system may be via computer networks, such as 154. Such a communication may be wired communication and/or wireless communication, local, such as between components which are located in the same room and/or remote, such as the communicating of geographically distributed components over the computer network 154. This communication may be access controlled and/or secured to protect the privacy of the user's data and the proper technical and/or clinical operation of the system. Control will be exercised on who can access which device and which function in the system. And control will be exercised on which device can communicate with which device.

Optionally, as shown at 160, a number of wearable monitoring apparatuses 100 are connected to a certain user. Optionally, one of the wearable monitoring apparatuses 100 of the same user may function as a master device that communicates with the components of the system as described above and concentrate data which is received from the other wearable monitoring apparatuses 100 of the same user. Optionally, the data which is acquired from wearable monitoring apparatuses 100 of the same user is managed and concentrated in by the user management unit 102.

Figure 3:
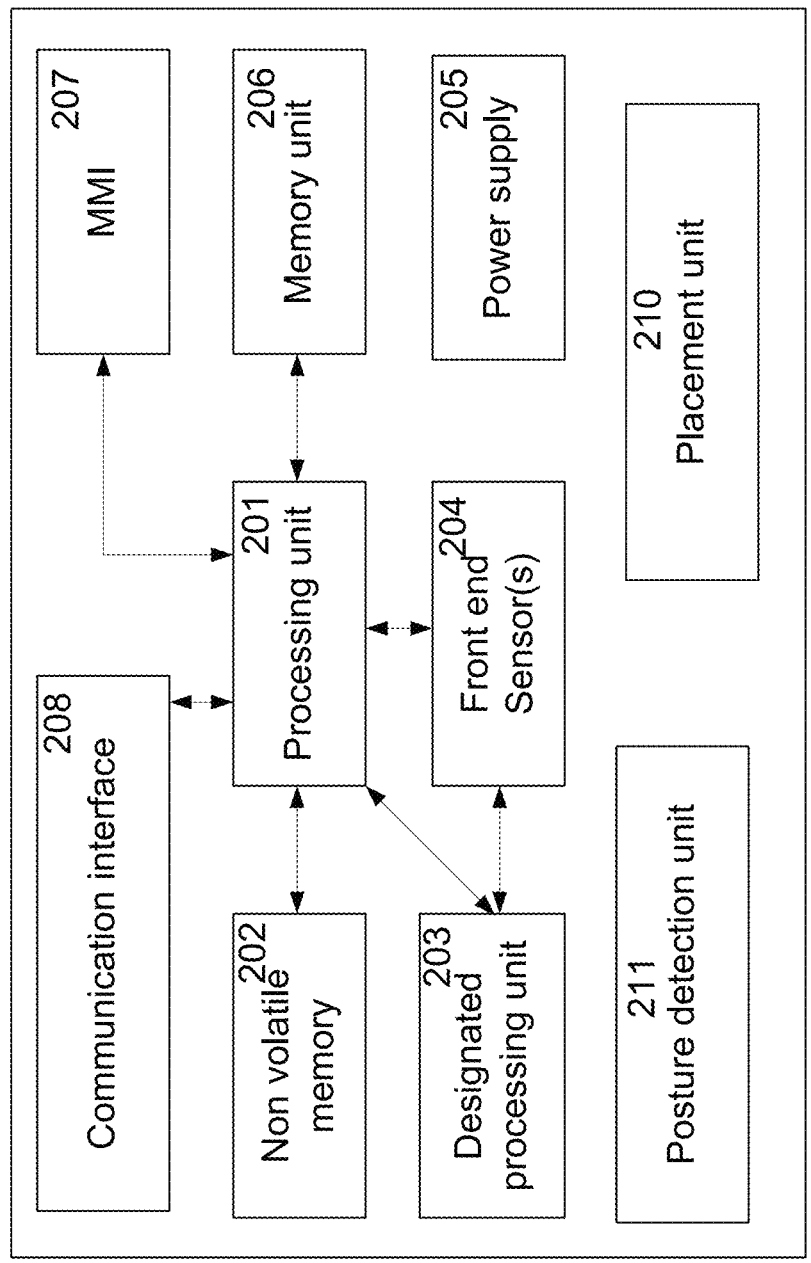
FIG. 3 is a schematic illustration of a set of components of an exemplary wearable monitoring apparatus, according to some embodiments of the present invention.

Reference is now also made to FIG. 3, which is a schematic illustration of a set of components 200 of an exemplary wearable monitoring apparatus 100, according to some embodiments of the present invention.

The exemplary wearable monitoring apparatus 100 which is depicted in FIG. 3 comprises a central processing unit (CPU) and/or a digital signal processing (DSP) which may be referred to herein as a processing unit 201. Optionally, the processing unit 201 runs a real-time operating system (RTOS) that is responsible for coordinating all functions of the monitoring device 100. The processing unit 201 is optionally used for analyzing the outputs of the one or more front-end sensors 204 which are described below. Optionally, the one or more front-end sensors 204 capture signals which are forwarded to the processing unit 201 that calculates medical indices of interest, which is optionally based on physiological, anatomical and/or clinical parameters. For example, the processing unit 201 may compare between the calculated parameters and a set of one or more predefined values and sets flags accordingly, for example as described below. The data which is calculated by the processing unit 201 is optionally used for generating one or more alerts and/or notifications, as further described below and in the co filed Patent Application. It should be noted, that the term processing unit means a local processing unit, a distributed processing unit, and/or a remote processing unit which is used for performing the functioning of the processing unit which is described herein. In an embodiment in which the processing unit is remote, the data which is forwarded to the processing unit is transmitted for remote processing by the remote processing unit.

The wearable monitoring apparatus 100 further comprises a memory unit 202, such as a non volatile memory, that is designed for storing the operating system and parameters which are needed for the functioning of the wearable monitoring apparatus 100. Optionally, the memory unit 202 is used for recording readings of reflections from the thorax and/or calculations which are based thereupon, for example as further described below. Optionally, as outlined above, the dielectric related properties of the monitored tissue, such as the fluid contents, for example pulmonary fluid contents which are calculated according to reflections of EM waves from the thorax, are recorded in the memory unit 202. Such a recording allows examining changes in the predefined and/or known biological patterns, such as in the pathological pulmonary fluid content, along a period that lasts between few hours and days, for example as outlined above. The recording allows calculating one or more baselines and/or the identification of a normal range which are adjusted according to the specific user. Optionally, the memory unit 202 is used for recording readings of medical sensors which are connected to the wearable monitoring apparatus 100 and/or embedded therein. Optionally, the memory unit 202 is used for storing additional information, such as application executables codes, configuration files for the processing unit 201, preset parameters, long term state parameters and tables. The memory unit 202 may be used for storing additional user related data, such as the user identification information, version information, user specific thresholds, authentication and/or security keys.

The wearable monitoring apparatus 100 further comprises a rapid access volatile memory unit 206, such as a dynamic random access memory (DRAM), a synchronous DRAM (SDRAM), and/or any other volatile memory for storing data that is needed to be accessed in a limited time for short terms. It may be interfaced by the processing unit 201, the below mentioned designated IC and/or any other component of the wearable monitoring apparatus 100.

Optionally, the wearable monitoring apparatus 100 comprises a designated processing unit 203, such as a designated integrated circuit (IC), for example an application-specific integrated circuit (ASIC) or a field-programmable gate array (FPGA) that contains logic blocks and programmable interconnects which are programmed to implement some of the functions required to process the data from the sensors front-ends. The designated processing unit 203 communicates with the processing unit 201, the memory unit 202, and/or with other components of the device for various tasks. Additionally or alternatively, the designated processing unit 203 may also implement any of the other blocks as an integrative solution. For example, the FPGA or ASIC may incorporate the processing unit 101 and/or another processing unit. Optionally, the logic blocks are programmed to implement monitoring methods as described in the co filed Patent Application.

As described above and depicted in FIG. 3, the wearable monitoring apparatus 100 further comprises one or more front-end sensors 204, such as EM transceivers, for transmitting a plurality of electromagnetic (EM) waves toward the thorax of the user and for capturing reflections thereof from an area of interest, such as the pulmonary tissues of the user 101. In some embodiment, the beam is transmitted in a desired pulse and allows the capturing of a reflection thereof from various areas on the surface of the user's body. Optionally, the capturing of a reflection is adjusted according a selected operational mode, for example according to a selected swept frequency, a selected frequency hopping chirp, and the like. Other modes and/or gating patterns according to which the beam is transmitted and allows the capturing thereof are described in the co filed application.

In such a mode, time gating may be used for focusing on a specific reflection, for example as described in the co filed Patent Application. The shape of the pulse may be generated using different shaping techniques.

In some embodiments of the present invention, the front-end sensors 204 include EM transducers which are designed for transmitting one or more pulses of EM radiation and intercepting the reflections of the EM radiation from monitored tissues and/or organs of the monitored user. Optionally, the monitored tissues are internal tissues, such as the pulmonary tissue. The intercepted reflection is converted to a signal having different features that allows evaluating dielectric related properties of the monitored tissues and/or organs, for example as described below. The EM transducers are optionally designed to continuously transmitting and analyzing the reflection for monitoring dielectric related properties of the monitored tissues and/or organs, which may be referred to herein, for brevity, as the monitored tissues.

Optionally, in order to achieve high range resolution while keeping the implementation relatively simple close range detection pulses are used. The shorter the pulse the higher is the space resolution. Such pulses are known in the art and therefore not discussed in great detail.

Optionally, the EM transducer is designed to transmit one or more stable frequency continuous wave (CW) radio signals and then to receive the reflection thereof from internal tissues and/or objects. The one or more CW radio signals may be transmitted, simultaneously or sequentially. For example, the CW radio signals may be transmitted in frequencies such as 900 MHz and 2.5 GHz. The CW radio signals may sweep one or more frequency ranges allowing measuring reflections in wide range of frequencies. CW signals reflections as well as any narrow band signal reflection may achieve high dynamic range by using narrow filtering around the used frequencies. The narrow filter may track the signal over time, for example, it may sweep together with the signal.

Optionally, the spatial and/or timing information is extracted by using multiple frequencies. Such information is mainly conveyed in the received phase of the signal. Optionally where a low number of frequencies which are not well spread over a large bandwidth results in a relatively poor or void time resolution. A single frequency allows generating differential measurements for measuring a movement and/or a displacement of a tissue and/or an organ by sensing a change over time of mainly the phase but also the amplitude of the received reflection. When a dielectric coefficient of a tissue and/or an organ changes, mainly the amplitude but also the phase of the reflection may respectively change. Multiple CW signals with spatial resolution thereof are indicative to a localized movement and/or displacement and/or dielectric changes.

As described above, the CW radio signals may be transmitted in one or more continuous or intermittent transmission sessions. In such an embodiment, known changes in internal organs may be used for performing differential measurements that may be indicative of dielectric coefficients of a monitored tissue and/or organ. Examples for physiological processes during which the changes in the internal organs are known may be heart beat cycle and/or a breathing cycle.

For example, the breathing cycle changes the dielectric coefficient of the pulmonary tissue. Such a change affects mainly the amplitude but also the phase of a CW signal which is reflected from the pulmonary tissue. A record that documents changes in the dielectric coefficient of the pulmonary tissue during at least one breathing cycle may be used as a reference for monitored tissues and/or organs, for example monitoring the fluid content in a monitored pulmonary tissue, for example as described in the co filed application.

In another exemplary embodiment, the dielectric coefficient of a pulmonary tissue may be monitored by tracking a differential measurement calculated based on the reflection from the interface between the lung and the heart during the systolic and diastolic phases of the cardiac cycle. As the movements of the heart are relatively rapid ~1 hertz (Hz) with respect to posture changes and movement, such a calculation reduce the effects of posture change and movement.

Reflections from the heart through the lung are changed, in phase and/or amplitude, during a systole diastole cardiac cycle. In some embodiments of the present invention, these reflections are used to evaluate a fluid content in a monitored pulmonary tissue. Thus, in order to improve the accuracy of this evaluation, the effect of the systole diastole cardiac cycle on the reflection has to be taken into account.

Changes in the phase and amplitude of reflections from the heart through the lung are indicative of dielectric related properties changes where the measurement itself is posture resilient. In particular, the phase of the systole-diastole differential measurement is indicative of a dielectric change in the lung. Changes in the concentration of fluids in the lung affect the phase velocity (EM radiation propagation speed) and therefore may be used for evaluating the fluid content in the lung. The amplitude of the differential signal is also indicative to dielectric change in the lung, as a pulmonary tissue with a certain concentration of fluids absorbs more of EM radiation that propagates therethrough than a pulmonary tissue with a lower concentration. The higher is the absorptions of reflections the lower are the reflections from the heart. Optionally, the reduced effect of the posture on the reflections is identified and further reduced using the posture detection methods which are described below.

In some embodiments of the present invention, the one or more EM transducers use a simplified narrow band and/or a multiple-band antenna, with one continuous band or several bands, which are matched to the monitored tissue and/or organ. Optionally, a placement mechanism or unit, such as the placement unit which is described below, is used for shifting the matching bands of the antenna according to the positioning thereof. Optionally, the CW signals are shifted each separately or jointly, so as to achieve optimal sensitivity to one or more parameter, such as shifts in respiration and heart rates.

Optionally, the CW signals referred to in this patent are equivalent to narrow-band signals, and all descriptions referred to such CW signals may be equivalently referred to the narrow-band signals. As used herein a narrow-band signal means a signal spreading over a small frequency band, for example up to 50 MHz, optionally modulated and used to expand the band of the transmitted energy. Such modulation may be frequency hopping, chirp, frequency-shift keying (FSK), phase-shift keying (PSK), amplitude Shift Keying (ASK) and the like. In such an embodiment, the EM transducers may de-modulate the reflections to compress the band back before further filtering and detection for improved sensitivity and dynamic range.

Optionally, the frequencies of the narrow band signals are 900 Mega Hertz (MHz) and/or 2.4 gigahertz (GHz) industrial, scientific, and medical (ISM) bands. Optionally, two frequencies, such as the aforementioned two frequencies, may be combined to improve time resolution and/or to separate reflections from neighboring interfaces, or may be used for improved sensitivity. In such an embodiment, the lower frequency penetrates deeper and less sensitive to small displacements. In such an embodiment, radiation in different frequency may be produced sequentially or simultaneously.

Optionally, narrow-band signals may be used jointly with pulsed wideband signals so as improve the overall sensitivity and robustness of the transmission session. As commonly known, a narrow band antenna is more directive and allow more power to be used for the narrow band signals. Optionally, the pulse wideband transmission may achieve improved spatial resolution while the narrow band signals may improve the penetration depth and extract information from deeper layers. Optionally, the one or more front-end sensors 204 includes additional medical sensors, such as an electrocardiogram (ECG), an electromyogram (EMG), ultrasound transducers, pulse oximeters, blood pressure sensors, accelerometers, tilt-meters, coagulometers, and optical blood saturation detectors.

In one example of the present invention, the wearable monitoring apparatus is attached to the skull of a user and used for monitoring a build up of intra-cranial pressure which may be a consequence of a head injury. The device may be focused on a specific location according to inputs from an imaging modality such as an MRI and/or a CT modality, either automatically and/or through a manual user interface. Alternatively, a broad region should be monitored either by a wide range of irradiated region from a single device or by a multiple transducers in a configuration as described below. The monitoring period is relatively short of few days, and the measurements frequency is relatively high specifically right after initial placement of every few minutes.

Figure 4A:
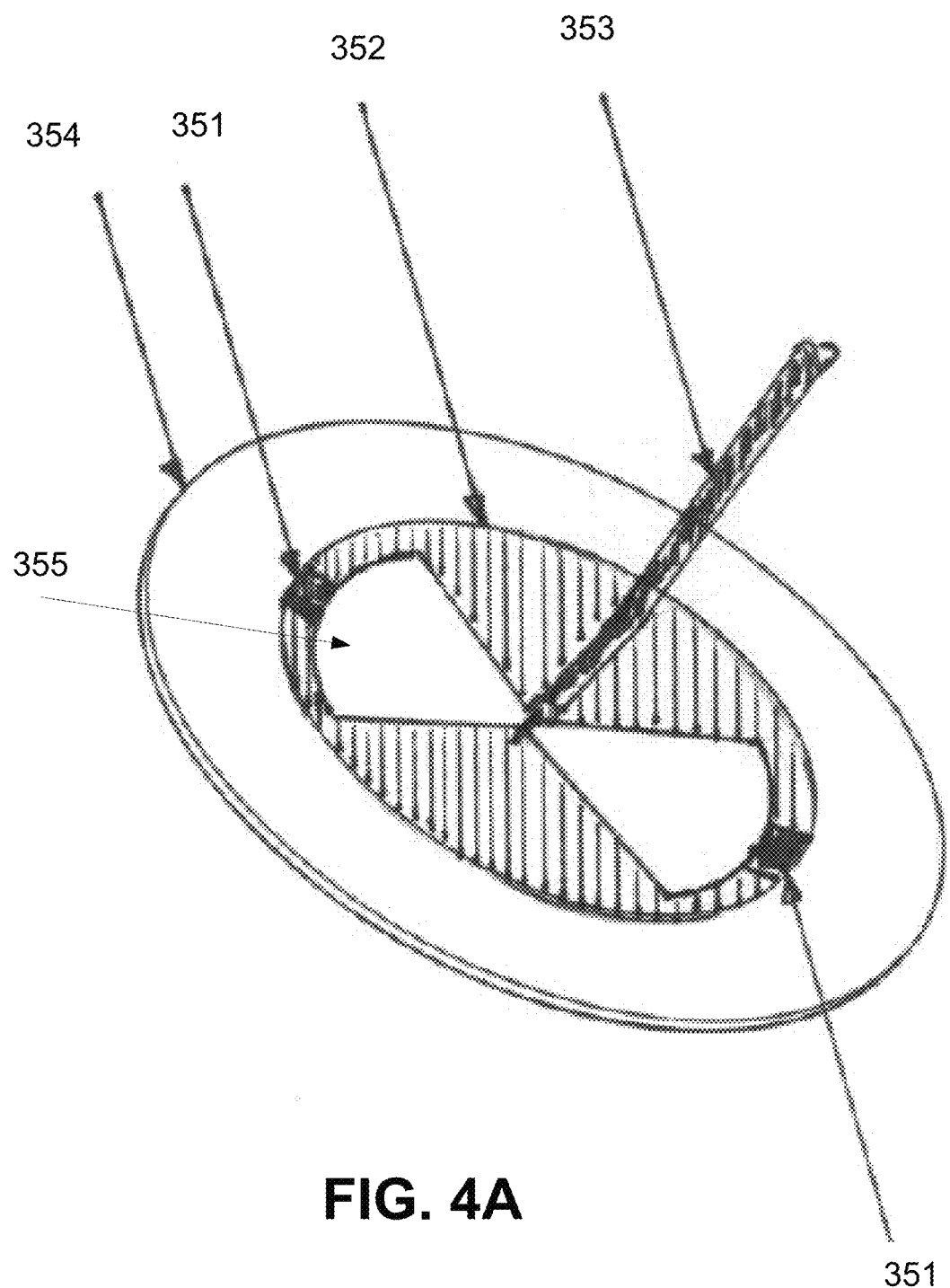
FIG. 4A is a schematic illustration of an exemplary EM antenna of an exemplary EM transceiver, according to some embodiments of the present invention.
Figure 4B:
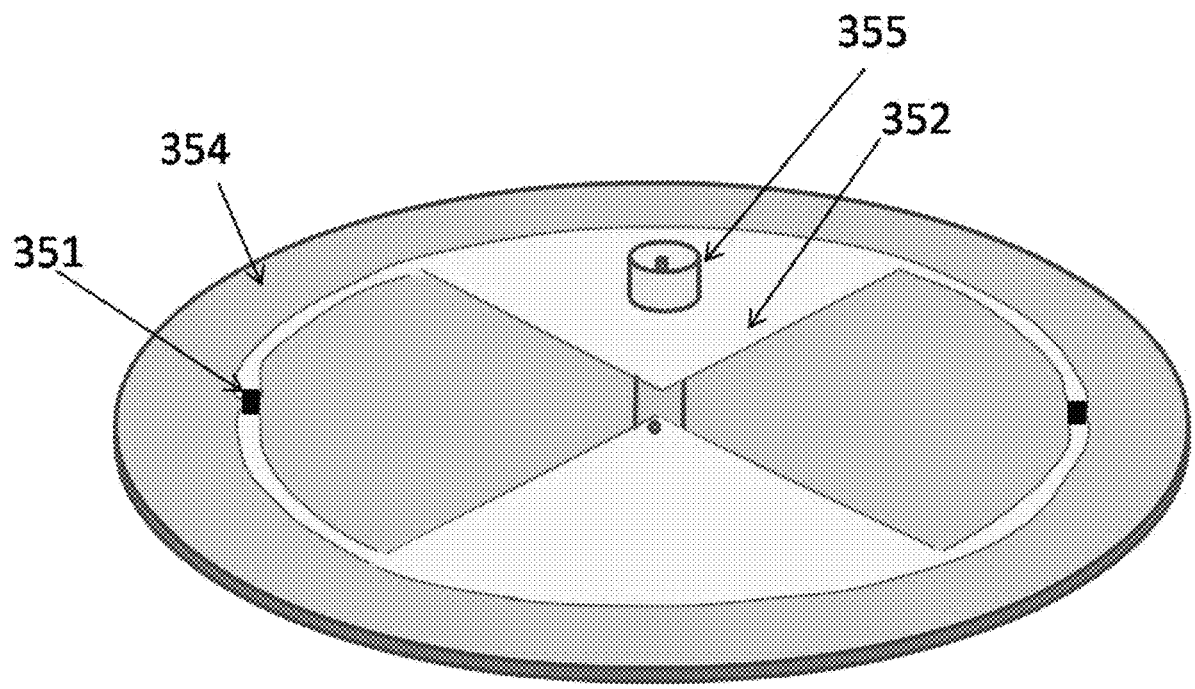
FIG. 4B is a schematic illustration of another exemplary EM antenna of an exemplary EM transceiver, according to some embodiments of the present invention.

Optionally, the one or more front-end sensors 204 include one or more EM transceivers which are designed for generating sharp pulses. Optionally, the EM transceivers are connected to and/or include one or more amplifiers, such as a low noise amplifier (LNA). Optionally, the EM transceiver having a slim profile that allows the manufacturing of a slim wearable monitoring apparatus 100, for example as depicted in FIGS. 4A and 4B.

Optionally, the EM transceiver is designed for sampling pulse signals which are echoed from an internal area in the body of the user, such as the pulmonary tissues, and indicative of the dielectric related properties of fluids, such as water, blood, and/or inflammation fluids therein.

Optionally, each EM transceiver utilizes one or more antennas for transmitting and/or intercepting EM signals. Each antenna may be configurable by setting antenna controls.

In some embodiments of the present invention, the antenna is a low reverberation antenna, such as a planar wide band antenna adapted for reducing the effect of reverberations upon the quality of signal transmission. Such an antenna produces a short duration fast-decaying pulses for improved time and range resolution. Optionally, the antenna terminates the radiation using lumped resistors to reduce reverberations, which may be referred to as re-ringing of currents, from the far end of the antenna and emulate an infinite antenna, without a need for printing tapered resistive layers.

Reference is now also made to FIG. 4A, which is a schematic illustration of an exemplary EM antenna 350 of an EM transducer, such as a transceiver, according to some embodiments of the present invention. In some embodiments of the present invention, the EM antenna 350 comprises resistors 351, which are optionally discrete resistors, a field transducer 352, a matching construction 353 and a dielectric substrate 354, which is optionally made of a flexible material and supports the construction of these components. The dielectric substrate 354 contains any flexible or non-flexible composite material, such as a polymeric film, paper, a fabric band, a rubber band, and a leather band.

Figure 4C:
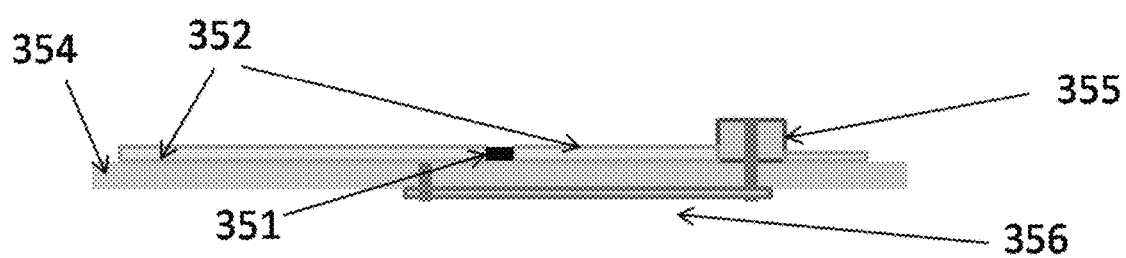
FIG. 4C is a lateral view of the exemplary EM antenna which is depicted in FIG. 4B, according to some embodiments of the present invention.

The field transducer 352, which is optionally metallic, is circular plate having a rounded biconic slot, which etched or engraved onto its surface. Optionally, the field transducer 352 is made of an electrically conductive material, such as metal and electrically conductive polymeric resins. Optionally, the rounded biconic slot 355 forms two round cones which are connected with two strips, such as extended strips, which may be supported by the dielectric substrate. In another embodiment, shown at FIGS. 4B and 4C, a connector, as shown at 355, such as a subminiature version A (SMA) connector, is used to connect the antenna and a transition line that leads the current to the center of the antenna. The circular plate is farther etched or engraved with two opposing gaps that allow the assembling of the resistors, such as lumped resistors, lumped coils, and/or lumped capacitors thereon. Optionally, the resistors are assembled between the two round cones at the opposing strips ends, for example as shown at 351.

As the EM antenna 350 comprises discrete resistors, printing of resistive layers may be avoided and the manufacturing cost of the EM antenna 350 may remain relatively low.

The structure of the exemplary EM antennas, which are depicted in FIGS. 4A and 4B, allows the transmitted electromagnetic energy to spread along the field transducer 352 with minimal or no disturbance. The electromagnetic energy that is not emitted from the EM antenna 350 is absorbed by the dielectric substrate 354 and optionally converted to heat.

In the antenna which is depicted in FIG. 4A, the matching construction 353 is optionally an unbalanced transmission line having an ungrounded conductor that carries electrical current from the power source connected at one apex of one of the round cones that comprise the biconic slot while a shield is continuously connected between the other apex of the other round cone and the rounded side thereof. The unbalanced transmission line is either pulled perpendicularly to the surface of the field transducer 352 or ended at the point in which the pulse transmitting and intercepting circuitry is assembled. Optionally, the unbalanced transmission line is embedded into a dielectric surface.

The arrangement that is depicted in FIGS. 4A and 4B reduce the ringing effect in low frequency band. As used herein the ringing effect means a distortion in the form of a damped oscillatory waveform superimposed on the main waveform of the EM wave that is captured by a respective transducer. For example, the EM antenna 350 which is depicted in FIGS. 4A and 4B have a reduced ringing effect and decays its pulse by additional −15 decibel (dB) after 1 nano second (ns) compared with bow-tie antenna.

It should be noted that such an arrangement allows the positioning of the EM field transducer 352 concomitantly to the body of the user. Such a positioning may soften the high back-scatter of energy that is caused by the antenna-skin interface that limits the dynamic range of the EM antenna 350.

Optionally, the antenna can be embedded within dielectric material to further decrease its dimensions or to expand its band to lower frequencies. As commonly known, a dielectric material improves the antenna performance by scaling of its dimensions. Optionally, the used dielectric material is a high dielectric material that slows the speed of light in an affective manner and allows a reduced size antenna. Such a reduced size antenna allows reducing the size of the wearable monitoring apparatus 100.

Optionally, the dielectric material is designed for separating the antenna from the skin and used to improve antenna-body EM wave penetration as well as reduce strong coupling between the antenna and the conductive skin. Optionally, the dielectric material is selected according to the thickness of the skin and fat layers of the user in a manner that reduces reverberations in these layers. In such an embodiment, the returning reflected pulse propagating to the antenna experiences a minimal impedance mismatch of the skin and minimal reflected power returns into the body for a sequential rounds.

Optionally, the antenna may be adjusted to the body impedance of a selected user by selecting matching resistors.

Optionally, the thickness of the EM antenna 350 is below 15 mm. Such a slim construction of the EM antenna 350 allows the generation of a slim wearable monitoring apparatus 100 that may be positioned on the surface of the user's thorax 101 relatively without affecting on the ability of the user to perform daily tasks, such as dressing, eating, and preparing meals. Optionally, the antenna can be curved to match the body part. The curving may be used to fix the antenna at a certain point on the body and reduce or eliminate its movements while the user moves.

Optionally, the EM transducers are adjusted for transmitting and intercepting EM radiation in intermittent data acquisition sessions, which may be referred to herein as transmission sessions. Optionally, the pace of the data acquisition sessions is constant. Optionally, the pace of the data acquisition sessions is random. Optionally, the pace of the data acquisition sessions, which may be referred to herein as a sampling rate, is adaptive. In such an embodiment, the data acquisition session rate, which may be referred to herein as a sampling rate, may be reduced when biological indications, which are monitored by the wearable monitoring apparatus 100, indicate that the risks for the monitored user decrease, for example when the monitored tissue is pulmonary tissue and it is less likely that the user develops cardiorespiratory decompensation. Similarly, the sampling rate may be increased when biological indications which are monitored by the wearable monitoring apparatus 100 indicate that the risks for the monitored user increase. Optionally, the sampling rate is determined according to the latest trend measurements. For example, if the case of slow rate of change of a monitored parameter in a given past period of time, the sampling rate me be reduced and vice versa. Optionally, the sampling rate is manually adjusted by the caretaker, optionally according to characteristics which are specific to the user. Optionally, the sampling rate is automatically adjusted, optionally according to one or more monitored biological indications, for example according to a ratio between the user's monitored biological indications and statistical data which has been gathered from monitoring other users, optionally with similar physiological characteristics and/or medical condition. For example, if the medical condition of the monitored user matches to a New York heart association functional (NYHA) class-3 user without pleural effusion, an electrical implantable device, such as CRT, ICD, and/or a pacemaker, and a renal deficiency, the sampling rate is set to a data acquisition session of 3 minutes every 6 hours. Optionally, the sampling rate is updated automatically, according to changes in the medical condition of the user.

In some embodiments of the present invention, the wearable monitoring apparatus 100 is designed for hosting and/or accessing a tissue model, such as the chest model, which is described in the co filed application, or other body part model. The tissue model may define the range of normal as well as abnormal dielectric related properties in different tissues, their dimensions and/or respective spatial configurations, and used in the analysis of the EM reflected signals as described above and below and in the co filed Patent Application, for example for detecting symptoms, predefined biological patterns and/or pathological patterns and/or changes, for example as described in the co filed patent Application.

Optionally, the wearable monitoring apparatus 100 is designed for eliminating the effects of the movements and/or changes of postures on the analysis of the measured EM reflected signals and determination of the biological parameter of the user. In some embodiments of the present invention, the wearable monitoring apparatus 100 is designed for gating the inputs of the one or more front-end sensors 204 for example as described in the co filed Patent Application. For example, the wearable monitoring apparatus 100 may be used for allowing the selection of reflection segments which are received from areas of interest having a static or dynamic location in relation to the wearable monitoring apparatus 100, for example as an outcome of physiological processes such periodical breathing cycle and/or heart beat pace, for example as described in the co filed Patent Application.

In some embodiments of the present invention the wearable monitoring apparatus 100 is designed for eliminating the effects of the movements and/or changes of postures on the analysis of the measured EM reflected signals and determination of a biological parameter of a user, for example as described in the co filed Patent Application. In such an embodiment, the wearable monitoring apparatus 100 comprises one or more posture detection sensors (not shown), such as accelerometers and tiltmeters, which provide data for classifying the current posture and/or activity level of the monitored user and/or for detecting a change on the posture of the user. In such an embodiment, the posture detection sensors may be connected to the processing unit 102 and utilize it for calculating the current posture and/or a change in the posture.

Optionally, the wearable monitoring apparatus 100 detects the posture of the monitored user and movements by analyzing the EM reflected signals as described below. In such an embodiment, data related to posture, movement, and/or activity of the monitored user may be used for identifying a period for performing a data acquisition session, such as the data acquisition sessions which are described below. In such a manner, biological indications, such as dielectric related properties, which are related to the monitored tissue of the monitored user may be acquired while the user performs an activity during which she is in high risk and/or while the data may be acquired in the most accurate and/or productive manner. For example, performing a data acquisition session may be triggered by the wearable monitoring apparatus 100 when the monitored user is undergoing high physical exertion and/or while the monitored user is at rest.

In some embodiments of the present invention the wearable monitoring apparatus 100 is designed for analyzing the EM waves which are received from the front end sensors 204 according to the frequency thereof. For example, high frequencies may experience changes resulting from a monitored physiological phenomenon, for example due to frequency dependent dielectric change. For example, fluid accumulation in the lung results in a stronger absorption of the higher frequencies. The frequencies may be analyzed according to wavelet transforms that provides frequency ranges and/or locality in time.

Optionally, the wearable monitoring apparatus 100 is connected to a power supply element circuitry 205 that is designed for generating and distributing the power supply that is required for the components of the wearable monitoring apparatus 100. The power supply element circuitry 205 comprises one or more batteries, optionally rechargeable.

Optionally, the wearable monitoring apparatus 100 comprises a man-machine interface (MMI) 207 for presenting data, such as an alert, a notification, statistical data, a current reading of the one or more front-end sensors 204 or external modality to the user, the user's caretaker, and/or others as desired. The MMI 207 may comprise a liquid crystal display (LCD), a touch screen, a speaker, a tactile generator, a set of light emitting diodes (LEDs), and/or any other indicator that may be used for presenting alerts and/or notifications which are based on a combination of the analysis of reflections of EM waves from an internal area in the body of the user, such as the pulmonary tissues, and indicative of the dielectric related properties of fluids, such as water, blood, and/or inflammation fluids therein and other parameters calculated based on the EM reflections and\or the integrated or external sensors. Optionally, the configuration of the wearable monitoring apparatus 100 may allows the user and/or a caretaker to define which alarm to present, for example whether the alarm is visual, audible, and/or tactile.

For example, when an alert is initiated as an outcome of the implementing of the aforementioned logic blocks the MMI 207 sounds an alert using one or more speakers and displays an appropriate message on an LCD display thereof.

Alternatively or additionally, an MMI 207 which is configured to perform the aforementioned functionalities is connected to a remote unit that communicates with the wearable monitoring apparatus 100, such as the aforementioned interrogator device 152 and/or any component of the user management unit 102.

Optionally, the MMI 207 and/or the MMI of the remote unit is connected to an input unit, such as a keyboard, a keypad, a touch screen and/or any other unit that allows the user, the user's caretaker, and/or others as desired to configure the wearable monitoring apparatus 100, adjust the MMI 207, make selections, and/or change modes of the MMI 207. Optionally, the MMI 207 and/or the MMI of the remote unit allows the monitored user to activate and/or deactivate the wearable monitoring apparatus 100, snoozing an alert, presenting the gathered data on which the alert is based, changing operational mode and the like.

Alternatively or additionally, the MMI 207 is configured for notifying the user when a battery replacement is necessary. Optionally, the MMI 207 uses the outputs of a placement unit 210, for example as described below, for guiding the user during the process of repositioning the wearable monitoring apparatus 100 after the battery replacement, for example by providing voice commands.

In some embodiments of the present invention, the wearable monitoring apparatus 100 is disposable. In such an embodiment, the MMI 207 may indicate to the monitored user when and optionally how to replace the wearable monitoring apparatus 100. Optionally, the placement unit is used for instructing the monitored user during the positioning of the wearable monitoring apparatus 100, for example but indicating to the monitored user when it is accurately positioned.

Optionally, the wearable monitoring apparatus 100 is integrated and/or designed to be integrated into a garment, such as a chest strap, a shirt, a vest, a hat, a sticker, pants, underwear and the like. Optionally, the wearable monitoring apparatus 100 is divided to disposable and reusable parts. The disposable part may include the battery, an attachment unit for attaching the wearable monitoring apparatus 100 to the body of the user, and/or any other electronic component that may be worn out by the use of the wearable monitoring apparatus 100.

Optionally, the wearable monitoring apparatus 100 is designed to perform, either automatically and/or according to a request from the user management unit 102, a maintenance activity.

Optionally, the wearable monitoring apparatus 100 comprises a communication module 208 that allows a user, a caretaker, and/or any other authorized monitored user to configure and/or update thresholds, user related data, and/or any other data which is related to the functionality of the wearable monitoring apparatus 100 from a remote client terminal or a communicating computing unit, for example via the user management unit 102, an interrogator device 152, and/or client terminal which is connected thereto. As used herein a client terminal is a personal computer, a cellular phone, a laptop, a personal digital assistant (PDA), and/or a Smartphone.

Optionally, the configuration comprises a set of initial parameters, such as the medical condition of the user, medical history related to the user, the age of the user, the severity of the user's condition, the weight of the user, the height of the user, an approximation of the user's chest diameter, and an indicator for one of the area selected for the apparatus. This configuration allows the adjusting one or more dynamic alert thresholds and/or any other characteristics of the alerting mechanism. Such an alert threshold may define the conditions for the activation of an alert for the user, the dosage control unit, and/or notifying a medical center about the data that has been gathered using the one or more front-end sensors 204. Several alerts threshold may be defined in a manner that allows a graded alerting, controlling a dose amount in a graduate manner, and/or notifying a severity of diagnosis, for example as described in the co filed application.

Reference is now made, once again, to FIG. 2. In some embodiments of the present invention, the remote client terminals 156, the medical data center 155, and/or the MMI 207 of the wearable monitoring apparatus 100 may be used for configuring the thresholds. Optionally, a technical communication channel is established between the remote client terminals 156, the aforementioned interrogator device, the aforementioned patient management unit, and/or the medical data center 155 and each one of the wearable monitoring apparatuses 100 and allows transference, optionally bidirectional, of data and/or instructions. In such an embodiment, the technical communication channel may utilize a caretaker to adjust the alerting thresholds. For example, a caretaker may be able to use a client terminal for adjusting a threshold for a user for whom false alerts are activated. In another example, the caretaker selects and/or changes an operational mode in a manner that may adjust the thresholds to the requirements of different routines, such as hospitalized mode, ambulatory mode, sleeping mode, and/or sport mode, unstable mode, and/or aggressive treatment mode. The term ambulatory may be used for describing different levels of motorial abilities, such as a partly ambulatory users which have the ability to walk freely in a limited pace and/or with a support, semi ambulatory users which have the ability to walk freely in a limited pace, and fully ambulatory which have the ability to walk, run, and/or jump freely, in various paces.

In some embodiments of the present invention, the remote client terminals 156, the medical data center 155, and/or the MMI 207 of the wearable monitoring apparatus 100 may be used for adjusting and/or defining the alerting mechanism. Optionally, the alerting mechanism is part is of the analysis of the outputs of the aforementioned front end sensors and/or biological information that is related to the monitored user, such as physiological, anatomical, and clinical data related to said user. Optionally, the multiple alerts are defined based on part and/or all of the data that is received from the front end sensors and/or medical databases and sources which are related to the user.

Optionally, the alerting mechanism is configured to trigger the presentation of an alert on the wearable monitoring device and in a set of plurality of different client terminals, medical centers and stations, such as the remote client terminals 156, the medical data center 155, the patient management units, the interrogator devices, and/or the MMI 207. The set of plurality of different devices and stations may be reconfigured by authorized members. New members, such as any client terminal of the user, a remote caretaker, a local caretaker, a selected family member, an affiliated person, a staff member of call center, a nurse, a and the like may be added.

Optionally, the alerting mechanism is designed for sending an email, an instant message, an MMS, an SMS, and/or any other digital content message for alerting the user and/or a caretaker. In such an embodiment, the user, the caretaker, and/or a system operator may enter an address identifier, such as a phone number, an email address, and/or an IM monitored user name to which the alerting messages will be sent. Optionally, the alerting mechanism is designed for triggering the alarm which may be put in a snooze mode by the user and/or the caretaker. For example, the user may snooze an alert indicated to him by an audible signal for duration of an hour. Once she has contacted her medical caretaker the caretaker may direct the user to increase his medication and snoozes the alert to different optionally longer durations.

Optionally, the wearable monitoring apparatus 100 comprises a communication interface 208 for establishing a connection, optionally bidirectional, with the user management unit 102, and/or with the interrogator unit. The connection allows the wearable monitoring apparatus 100 to transfer that data that is stored in the memory unit 206. Optionally, the communication interface 208 is based on wired connection, for example a universal serial bus (USB) interface. Alternatively or additionally, the communication interface 208 is connected to a wireless data interface, such as an example an infrared (IR) interface, a wireless fidelity (Wi-Fi) interface, a Bluetooth™ module, a electromagnetic transducer module, a universal asynchronous receiver transmitter (UART) and the like. Optionally, the connection allows the wearable monitoring apparatus 100 to report on a malfunction in one of one or more front-end sensors 204 and on any other malfunction in the monitoring of the dielectric related properties of fluids in an internal area of the user's body's, for example in the pulmonary tissues of the user 101. Optionally, the communication interface 208 is used for supporting the configuration of the device, for example by allowing the uploading of state parameters, version control software elements for updating firmware and software components, and for reporting current and recorded information such as clinical parameters such as heart rate, breathing frequency, edema condition, and/or any parameter measured by one of the aforementioned sensors, and any parameter or data calculated based thereupon.

Optionally, the wearable monitoring apparatus 100 is designed to communicate with the user management unit 102 and/or an interrogator device 152, as outlined above and described in the co filed Patent Application.

Optionally, the wearable monitoring apparatus 100 is connected to a dosage control unit (not shown). The dosage control unit may be integrated, in a detachable or fixed manner, into the wearable monitoring apparatus 100. Optionally, the dosage control unit is designed to control the dispensing of a medication. Optionally, the wearable monitoring apparatus 100 is designed to generate a treating dosage recommendation according to the measured dielectric related properties, vital signs, and/or any other data which has been captured by the front end sensors or available otherwise. The treating dosage may define a change in the quantity and/or frequency of a certain treatment. Optionally, the wearable monitoring apparatus 100 changes the manner the dosage control unit controls the dispensing of a medication according to the defined change and/frequency.

Optionally, the wearable monitoring apparatus 100 is connected, optionally wirelessly to a control unit (not shown), such as a valve in a system for assisted ventilation of patients and for administration of anesthetic gas, based on the estimations of the breathing depth and the degree of the independent respiration muscle operation. Examples of ventilation techniques include positive airway pressure (CPAP), assisted or controlled ventilation and intermittent mandatory ventilation, among others. In use, the patient's lungs are ventilated by cycling airway pressure between ambient atmospheric pressure and some higher ventilation pressure. During the high pressure phase of the cycle, the lungs are inflated with the breathing gas mixture supplied by the system. During the ambient pressure phase, the lungs deflate as the patient spontaneously exhales the gas into the atmosphere or other suitable exhaust facility. Optionally, the valve control unit is designed to control the opening and/or closing of the valve and/or the size of its orifice. Optionally, the wearable monitoring apparatus 100 is connected, optionally wirelessly to an implanted medical device. In such an embodiment, the communication interface 208 may be used for transmitting and/or forwarding instructions to the implanted medical device according to the detected change, for example according to a detected change in dielectric related property.

Optionally, the dosage control unit is designed to control or provide a feedback to treatments in oncology, such as irradiation therapy, chemotherapy, anti angio-genesis therapy, and the like. In such an embodiment, the communication interface 208 may be used for transmitting and/or forwarding instructions to the dosage control unit and/or to a presentation unit that present a recommended dosage and/or medicament to the user and/or to a treating medical personnel. Optionally, the dosage control unit is designed to provide data regarding the effectiveness of the treatment in the current posture of the patient and/or placement of the wearable device, and providing a feedback regarding the frequency of the treatment and the dosage in use. Moreover, it may be used to provide a feedback regarding the peripheral damage to a normal tissue as a consequence of the treatment. This feedback may be used for directing instructions and may be based on the dielectric related properties, changes and/or patterns which are calculated by the designated processing unit 203, according to intercepted reflections and integrated and external sensors.

Optionally, the wearable monitoring apparatus 100 communicates, optionally wirelessly, with one or more other wearable monitoring apparatuses which are used for monitoring dielectric related properties of fluids in other internal tissues of the body of the monitored user.

Figure 5:
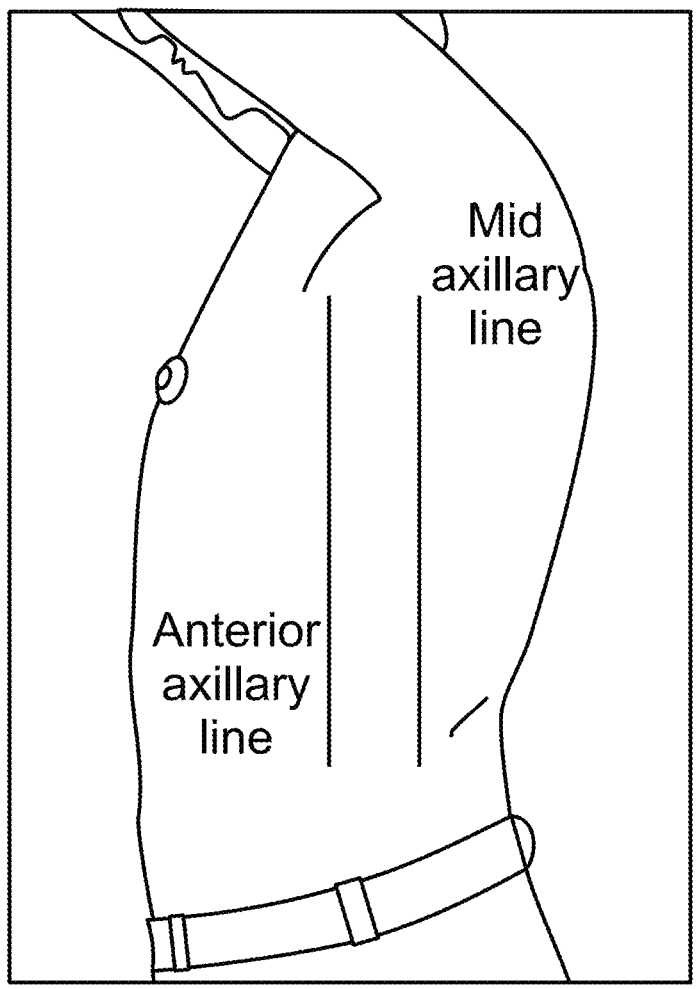
FIG. 5 is a schematic illustration of a right mid axillary line in which the wearable monitoring apparatus may be positioned, according to some embodiments of the present invention.

Optionally, the wearable monitoring apparatus 100 may be placed in several positions in relation to the user's thorax 101. A location for positioning the apparatus may be selected such that the pulmonary tissues are monitored during a full breathing cycle of the user 101. For example, the position may be in front of the fifth and sixth ribs, at the right mid axillary line, for example as shown at FIG. 5. It should be noted that positions in which the lungs wall is monitored in portions of the breathing cycle may also be selected.

In some embodiments of the present invention, the wearable monitoring apparatus is designed to beam different areas of interest of the thorax from different angles. Optionally, the wearable monitoring apparatus includes a number of different antenna elements which are spaced from one another. Such a spatial diversity allows separately focusing on one or more of the areas of interest and improves spatial and time separation in transmission and/or reception.

Optionally, the ROI may change according to one or more physiological activities such as breathing. Optionally, a tracking mechanism is used to adaptively change the phase and amplitude of one or more of the antenna elements. Measurements of two or more areas may improve relative measurements which are used as an informative feature for posture cancelation and/or physiological parameter extraction, as explained below.

Optionally, a number of transducers are directed to capture reflections from a common tissue. In such an embodiment, the captured reflections may be combined for improving the lungs dielectric coefficient sensitivity.

Separating the angle of transmission from the angle of reception reduces effects of undesired near antenna changes, such as movements and posture changes. The reception from a transmission path results in a relatively strong reflection from the near antenna layers. A change in such a layer may override important information from an internal tissue in the body. Two or more transmitting and receiving elements may reduce the strength of the reflection received from layers which are close to the antenna while giving more weight to reflection from the internal tissues.

The positioning of the number of different antenna elements may be adjusted for specific suspected pathologies. For example, for monitoring co-morbidities of heart failure and chronic obstructive pulmonary disease (COPD), designated antenna may be located in front of the right upper pulmonary segment and the lower left pulmonary segment. Such antenna elements allow the detection of differences of congestion levels between different segments, for instance by a function of posture and/or activity which may assist in the diagnosis of the current etiology of the fluid congestion.

Reference is now made, once again, to FIGS. 1 and 2. In some embodiments of the present invention, the wearable monitoring apparatus 100 is designed for detecting the posture and/or the activity of the user, thereby to generate clinical parameters that take into account the posture of the monitored user.

Figure 6A:
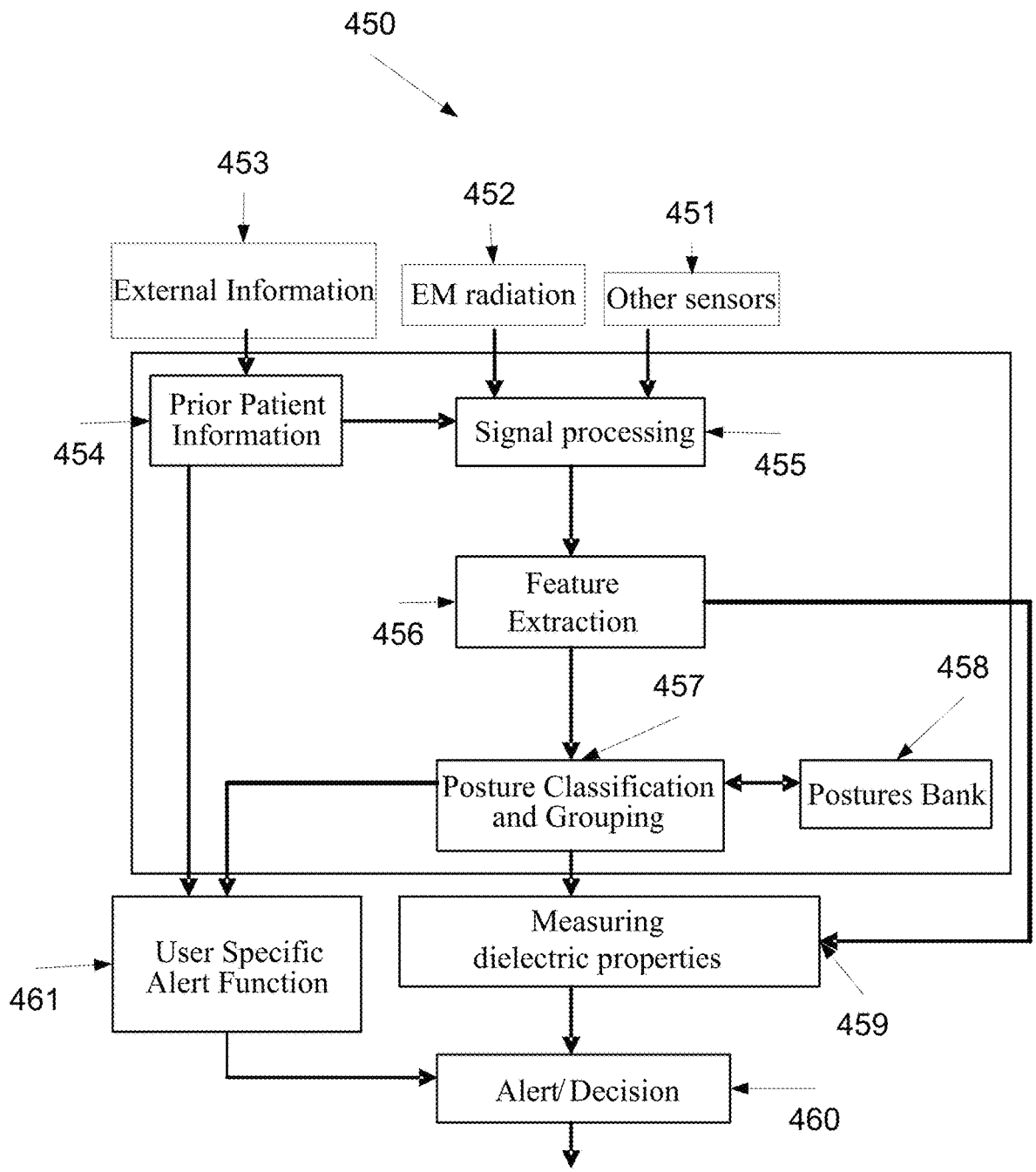
FIG. 6A, is a flowchart of a method for using EM radiation for detecting a posture of a user, according to some embodiments of the present invention.

Reference is also made to FIG. 6A, which is a flowchart 450 of a method for using EM radiation for alerting a user, and the posture detection block 450 detecting a posture of a user, according to some embodiments of the present invention. FIG. 6A depicts, inter alia, exemplary modus operandi of the posture detection unit 211, which is depicted in FIG. 3.

Optionally, the wearable monitoring apparatus 100 is designed for identifying postures based on dielectric related properties of internal organs and/or tissues as extracted from the analysis of the EM reflected signals and/or other outputs of other sensors. In the EM-based posture detector case, posture may be defined as the relative position of the radiating element and monitored internal or external organ. As shown at 452, data from the one or more EM transducers is received at the wearable monitoring apparatus 100. Optionally, additional data 441 from the front end sensors 204 and/or from external data sources 443, such medical data about the user from medical databases is gathered. As shown at 454 the medical data may be stored and/or received from the memory of the wearable monitoring apparatus 100. The data 441-443 may be received simultaneously, sequentially and/or interpedently.

Optionally, the EM radiation 442, such as the aforementioned reflected signals, and the additional data 441, 443 is processed, as shown at 455 to allow the extraction of features therefrom, for example as shown at 456. A feature may be based on the morphology and/or timing of the received EM signals. For the posture detection functionality features indicative to the posture are extracted, such features may include for example the reflected signal gated to the near-antenna layers reflections, assumed to have strong posture indication. Other features are extracted for the purpose of measuring the dielectric related properties of the desired organ and used in 459. These features are indicative to the measured tissue and/or organ dielectric related properties. Some of them are sensitive to posture changes and some are more resilient. Examples of features that may be used for posture classification and acquired by analyzing reflections of EM radiations are morphologies reflections, amplitudes, positions of peak of signals from reflections of selected tissue boundaries, such as fat-muscle, lung-heart, and muscle-lung, differences of amplitudes in signals which are based on reflections and/or peak positions, either among different segments of the signal or between signals measured at different time instances, for example amplitude difference of the reflection received from lung-heart boundary in a signal measured in the time instance of contraction, compared to a signal measured in the following relaxation; or similarly for the muscle-lung boundary during end-expiratory and end-inspiratory time instances. Optionally, frequency domain features may be extracted from the EM reflection, like amplitude and phase response of a gated signal, where the gating may localize a reflection from a specific interface between tissues. In some embodiments one or more features may represent EM reflections of narrow band signals, described earlier, like phase and amplitude. Optionally, one or more features may represent information extracted from the external sensors.

As shown at 457, the extracted features may be used for classifying the posture of the monitored user. In use, the current posture of the monitored user may be found by a match between signals received from the one or more EM transducers and/or an analysis thereof and a value, a feature, a pattern, and/or a range from a posture bank 458.

Optionally, the posture bank 458 includes a scale of values, or a range of values, of exemplary features, and/or a combination of features. Optionally, the each value or range in the scale is associated with a tag of a selected posture. Optionally, during the classification the identified features are matched with the class values in the scale. The matching may be performed using known matching methods. Optionally, each class value is generated using known supervised and unsupervised learning algorithms. These matching, clustering and/or classification algorithms are known in the art and therefore not elaborated herein in greater detail.

Optionally, the posture classifier and grouping, 457, may output soft decisions like the probability of each known posture to be the current posture. Its output may be regarded as a feature for any following classifier or estimator, such as the measuring dielectric related properties block 459.
Features which are posture resilient can be used to relax the demands from the posture detector and achieve improved dielectric related properties and measurement sensitivity. Such features are required to be highly sensitive to measured tissue and/or organ dielectric related property, while being less affected by other changes like posture changes. For example, features extracted from differential signals, where differential signals are referred to as the differences between two or more signals measured during a short period of time as elaborated above.

Different postures may be identified according to their effect on the pattern of signals which are reflected from different areas in the body. In one exemplary embodiment the wearable monitoring apparatus 100 is used for measuring dielectric related properties of the pulmonary tissues, for example as described in the co filed application, and the extracted feature is the position of the highest peak in a differential signal based on EM radiation reflected from the thorax. In this exemplary embodiment, the position of the peak is indicative of a relative position of the muscle-lung boundary and therefore may be used for classifying the posture of the user. Optionally, the amplitude of the same peak may be used as a feature for measuring the dielectric related properties of the lung, due to its sensitivity to the dielectric coefficient of the lung.

Optionally, the posture detection based on the EM reflection from an exit boundary between tissues. This may promote the sensitivity and robustness for the measurement of the dielectric coefficient of the measured tissue due to the propagation of the EM radiation in and out the measured organ as well being reflected from a reference tissue and/or organ. For example, measuring a differential signal between the systolic and diastolic phases, and analyzing the reflection from the lung-heart interface.

The posture detector is used for reducing changes to the EM reflections due to dielectric related properties changes as a consequence of postures changes. In some aspect of the invention this functionality of the posture detection may be referred to as posture compensation. In some embodiments of the present invention the posture detection is based on a tissue model which has been adapted according to the reflection signals. Optionally, the expected reflection signal is used as a baseline and a difference between the baseline and a signal which is based on the actual measured reflections is analyzed to extract changes and/or values which are related to the dielectric related properties of the monitored tissue and/or organ. dielectric related properties. Optionally, the estimated model is calculated according to data acquired by EM sensor a non EM sensor, such as an ultrasound imager, computerized tomography (CT) and/or magnetic resonance imager (MRI). The model is a simplified one-dimensional, a two dimensional (2D), three dimensional (3D) model and/or four dimensional model and so on and so forth. The estimated model may be used for compensating for the posture effect prior to the processing of the signals 455, and/or prior to the feature extraction 456, and/or prior to the posture classification and clustering block 457 and/or the measuring of dielectric related properties 459. The model based posture compensation can reduce posture effect on some or whole of the measured reflection signals, therefore, improving posture detection statistics and reduces posture variance.

In some embodiments of the present invention, as shown at 459 and described above, the wearable monitoring apparatus 100 measures and/or monitor dielectric related properties of internal tissues and/or organs according to segments of a signal that is based on reflections from tissue boundaries of the monitored tissue and/or organ and/or other reference internal tissues and/or organs. These signals may be monitored over a period and/or in multiple discrete instances or in a single instance. As described above, the posture classification 457 may be used for reducing and/or removing the effect of the posture on the calculations which are based on the dielectric related properties of internal tissues and/or organs. In such a manner, alerts and/or the reports which are based on the dielectric related properties, for example as shown at 460, may take into account the effect of the posture of the user. In such a manner, the number of false alerts may be reduced and the reports may provide a more accurate and complete presentation of the medical condition of the user. Optionally, user specific alert are also generated according to the posture detection, for example with respect to a treatment which is adjusted for the user. In such an embodiment, the device may be used for monitoring the movement of the user and to reduce harm that the user may cause to her, to the progress of a given treatment, and/or for a monitoring process by the biological probe.

The detection of the posture of the monitored user allows taking into account the effect of the posture on the dielectric related properties of the monitored pulmonary tissue, for example by normalizing the values. In such an embodiment, the aforementioned biological parameters reports and/or alerts do not ignore the effect of the posture of the user on the measured clinical parameters.

In some embodiments of the present invention, the posture detection is used for guiding the monitored user to get into at an optimal, or substantially optimal, posture before and/or during a monitoring session. Optionally, the guiding may be used for instructing the user to change posture in an automatic diagnosis and/or treatment that is performed by the wearable monitoring apparatus 100 and/or another monitoring apparatus. Optionally, the MMI 207 implements an interactive process during which the user tunes her posture until reaching the optimal, or substantially optimal, posture and/or moves through several postures.

Optionally, the MMI 207 includes a minimal monitored user interface, such as a single push button and/or minimal number of audible and/or visual signals.

For brevity, all the features and embodiments which are described herein with regard to the wearable monitoring apparatus 100 may be used by the posture detection unit when used for detecting postures of users that wear other wearable elements and/or probed by various biological probes.

Figure 6B:
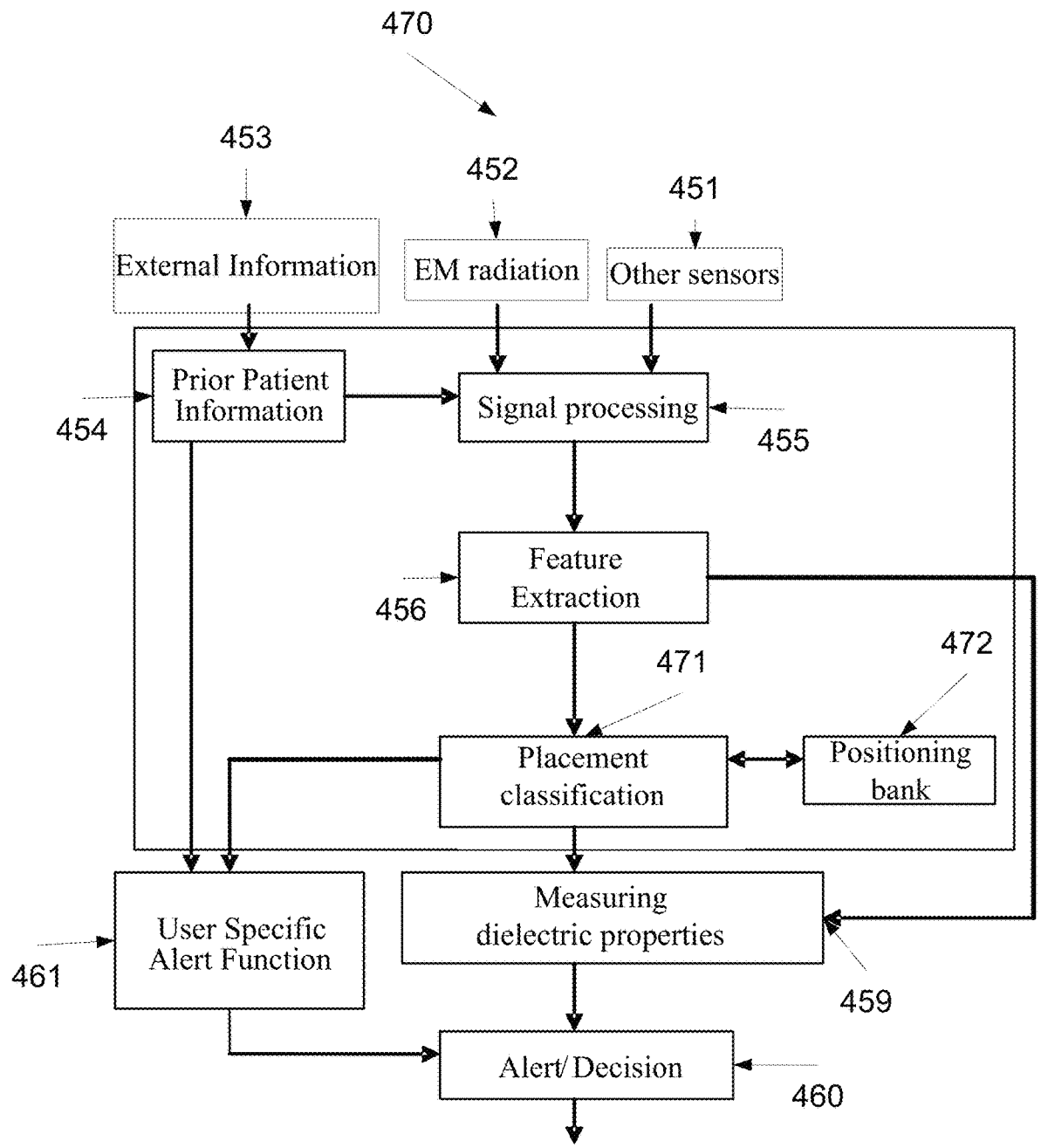
FIG. 6B is a flowchart of a method for using EM radiation for detecting the placement, misplacement and/or disengagement of a biological probe, according to some embodiments of the present invention.

Reference is now made to FIG. 6B, which is a flowchart 470 of a method for using EM radiation for detecting the placement, misplacement and/or disengagement of a biological probe, such as the wearable monitoring apparatus, according to some embodiments of the present invention. FIG. 6B depicts, inter alia, exemplary modus operandi of the placement unit 210, which is depicted in FIG. 3. Blocks 450-461 are as described in FIG. 6A, with respective changes for placement, misplacement, and/or disengagement monitoring and/or detection. However FIG. 6B depicts few functions and/or processes which are related to misplacement and/or disengagement of a biological probe.

Optionally, the wearable monitoring apparatus 100 comprises a placement unit 210 for monitoring the positioning of the wearable monitoring apparatus 100 on the body of the user. Such a monitoring allows detecting a displacement of the wearable monitoring apparatus 100 and/or alerting the user and/or a remote caretaker when the wearable monitoring apparatus 100 is displaced and/or intentionally and/or unintentionally changes a position.

It should be noted that such a placement unit 210 may be used for monitoring placement and/or displacement of various monitoring and therapeutic devices, such as imaging modalities, for example ultrasound imaging modalities, stationary and/or mobile biological probes, and/or any other monitoring device which the positioning thereof on the body of the patient has an effect on the receptions and/or outputs thereof. In such an embodiment, the placement unit 210 comprises a memory element, such as the memory element which is depicted in FIG. 3 and described above, for storing one or more reference values each indicative of exemplary reflection of EM radiations delivered to the monitored internal tissue of the user and/or one or more exemplary dielectric related properties. Optionally, the reference values are stored in a positioning bank, for example as shown at 472. Such reference values, which are optionally ranges of values, represent the values which are supposed to be reflected from the monitored tissue. The placement unit 210 comprises and/or connected to one or more EM which deliver, from the monitored wearable element, EM radiation and intercept the actual reflection thereof. The placement unit 210 comprises processing unit and/or configured to use the processing unit of the monitored wearable device. The processing unit is used for identifying and/or classifying the misplacement, placement, and/or disengagement, as shown at 471, optionally by comparing between the reference value and the actual reflection. For brevity, all the features and embodiments which are described herein with regard to the wearable monitoring apparatus 100 may be used by the placement unit 210 when used for monitoring the placement and/or displacement of other wearable elements and/or biological probes.

Optionally, the placement unit 210 is used for monitoring the initial placement of the wearable monitoring apparatus 100. Optionally, the placement unit 210 is used for monitoring the positioning in a periodic or continuous manner. Optionally, as depicted in 460 the placement unit 210 is designed for alerting the user and/or a medical center when disengagement and/or an improper functioning of the wearable monitoring apparatus 100 are detected. Such an improper functioning may be an outcome of a low power, a system failure, and/or corrupted and/or unintelligible readings of the one or more front end sensors. For example, if disengagement is detected, the MMI 207 is instructed, optionally automatically, to alert to the user and/or a medical center. Optionally terminate other functionalities of the device, such as transmission and/or reception shut down. This functionality enables avoiding undesired EM emissions to air and a situation in which the device is not properly coupled to the body. If the placer identifies a suspicious change in reflection it may terminate transmission sessions or reduce power to the minimum required for detecting reflections from layers which are positioned in proximity to the antenna. When the reflection from these layers matches to an expected reflection, the transmission power may be raised gradually.

The placement, misplacement and/or disengagement detection, which may be referred to herein, for brevity, as placement detection, is based on the detection of an unexpected change and/or an irregular pattern. Optionally, one or more control patterns and/or values are defined as features in 456, in order to allow the monitoring of the disengagement detection.

Optionally, the disengagement is detected when the pattern of features extracted from the received reflections from the front end sensors 204 substantially differ from the pattern of features which is expected to be received at the position of the wearable monitoring apparatus 100. As described above, the wearable monitoring apparatus 100 is designed to be positioned in one or more areas. The configuration of the wearable monitoring apparatus 100 allows the user and/or a caretaker to enter the position of the wearable monitoring apparatus 100. This position may be used for selecting a model, such as the wall chest model that is depicted and described in the co filed Patent Application that is adapted thereto.

In such an embodiment, the disengagement is detected if the data which is received from the front end sensors 204 does not match the adjusted model.

Optionally, the disengagement and/or misplacement is detected when the data which is received from the front end sensors 204 does not express an expected physiological process, such as a breathing cycle, the pace of the heart beats, and/or any other process that have detectable effect on the backscatter of EM waves which are emitted toward the front end sensors 204. For example, when the front end sensors 204 are attached to the chest, it is expected that the acquired signal is modulated by the breathing cycle which affects the dielectric coefficients of the lung.

Optionally, the disengagement and/or misplacement are detected when the data which is received does not match a set of reference records. In such an embodiment a set of reference records is recorded, automatically and/or manually, after a proper positioning of the wearable monitoring apparatus 100. The recorded set of reference records is used for generating a reference pattern that a deviation therefrom may be used for detecting disengagement.

Optionally, the disengagement and/or misplacement are detected when the data which is received does not match a predefined range of values defined for each feature.

Optionally, the placement unit 210 is designed to report the positioning of the wearable monitoring apparatus 100 and/or the accuracy of the positioning of the wearable monitoring apparatus 100 to a remote client and/or server, for example using the aforementioned technical communication channels, which are described in relation to FIG. 2.

Optionally, the placement unit 210 estimates the quality of the positioning in reference to prior measurements recorded in memory or expected reflections. It may measure specific features and compare them to the references or the actual measurement. It then notifies the user and the algorithm of its findings.

A manual search for the correct position may include sliding the device in different directions on the body until a fixed visual and/or audible is heard. Optionally, the placement unit 210 is connected to a mechanical adjustment unit for automatically changing the position of the wearable monitoring apparatus 100, the one or more transducers thereof and/or any other biological probe, in relation to the body of the user. The mechanical adjustment unit may include an actuation unit that comprises one or more motors, gearwheels, and ratchets for automatically adjusting the extended strips, and/or any other attachment elements which are connected to the wearable monitoring apparatus 100.

In some embodiments of the present invention, the monitoring is performed by placing the apparatus for short period repetitive monitoring sessions, for example a monitoring session of 5 minute measurement a once, twice, and or three times a day.

It should be noted that the posture and/or the engagement, placement, and/or misplacement processes may be used during the calculation of values which are related to intervening tissues, for example for normalizing their values.

In some embodiments of the present invention, the monitoring apparatus is designed as disposable device which is designed to replace and/or being replaced by a similar monitoring apparatus and/or with a placement unit that allows repositioning it after performing a maintenance activity, such as replacing a battery and/or cleansing. In such embodiments, the monitoring apparatus is designed to be placed and/or replaced, optionally a number of times, in a predefined position in relation to a reference internal tissue of the body of the user. In some embodiments, the monitoring apparatus may be wearable, as shown at 100, and/or designed to be taken off intermittently, for example, for convenience reasons and/or for allowing the replacement and/or fixing of a component due to wearing-off of the package, an adhering material used for attaching the monitoring apparatus or a portion thereof to the body, and/or a battery. As described above, the functionality, configuration, and/or use case of the monitoring device may depend also on user posture and/or internal tissue position. For example, a biological sensor such as the EM pulmonary content fluid sensor described in herein and in the co-filed patent application.

During a placement processing, the posture detection unit may use prior posture positioning data, optionally stored as records of the aforementioned posture bank 458, as reference data indicative of the position to which the posture detection unit should be replaced.

Optionally, the placement unit may detect a misplacement of the device after being worn, for example, due to movements of the user and/or wearing off of the glue. Where the placement unit may alert the device or the user upon misplacement and/or eliminate or reduce radiating EM power so as to avoid interferences.

Optionally, the placement unit may be designed to receive historical positioning data that is used as a reference point during the placement and/or replacement process. The historical positioning data may be received via a wireless and/or a wired connection with a similar monitoring apparatus which is replaced by the monitoring apparatus housing the placement unit and/or from a information originating from the replaced monitoring apparatus which has been saved in the patient management unit or elsewhere and/or from the position bank 472 which is depicted in FIG. 6B. In such a manner, historical positioning data may be generated by the similar and/or housing monitoring apparatus before the replacement and forwarded to the placement unit to allow the placing and/or the replacing of the monitoring apparatus as described above.

Figure 7:
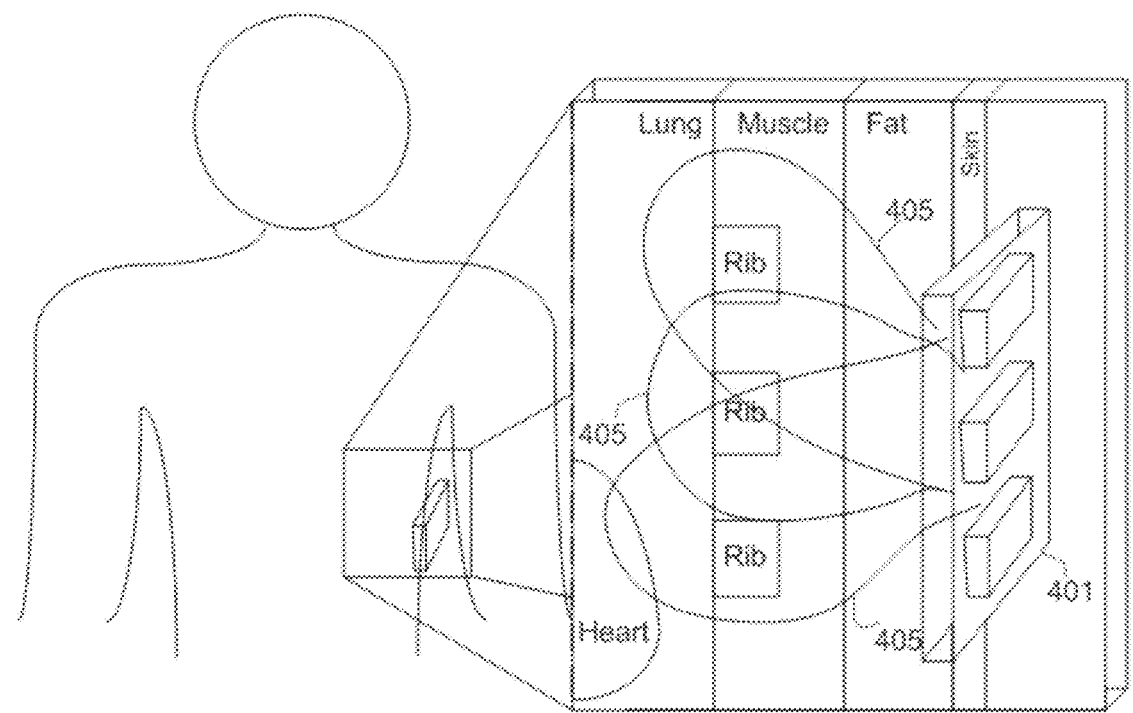
FIGS. 7 and 8 are schematic illustrations of a wearable monitoring apparatus with a plurality of transducers designed for beaming and/or capturing EM waves, according to some embodiments of the present invention.
Figure 8:
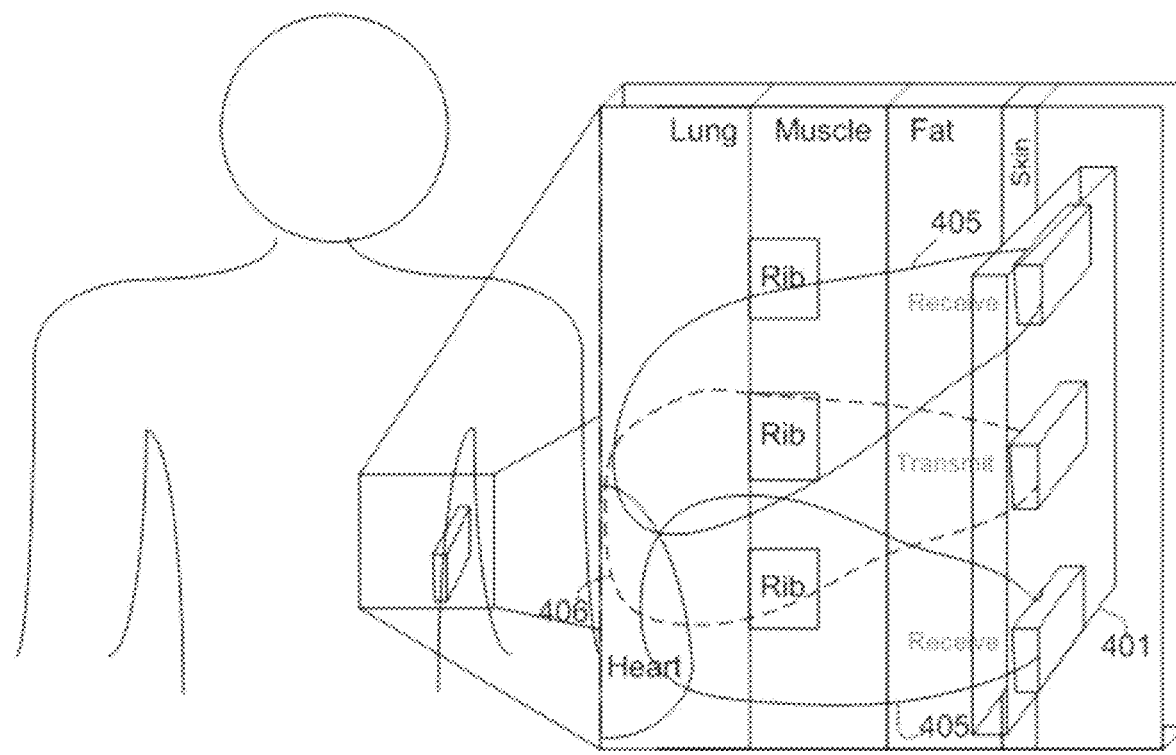

Reference is now made to FIGS. 7 and 8, which are schematic illustrations of a wearable monitoring apparatus 100 with a plurality of transducers for beaming and/or capturing EM waves, according to some embodiments of the present invention. FIG. 7 depicts a wearable monitoring apparatus 100 with an array of transducers 401 that is designed for transmitting EM signals capturing its reflections from a plurality of different directions. FIG. 8 depicts a wearable monitoring apparatus 100 with an array of transducers 401 that includes separate transducers for capturing reflections from the tissues 405 and separate transducers for transmitting EM waves toward the tissues 406. The different elements may be located in proximity to one another or spread over different locations, in a similar manner the elements can have the same pointing direction or can have different pointing directions. For example, one antenna element may be placed on the back of the user, another on the side and third on the front of the user thorax. In the group of antenna elements which are depicted in FIGS. 7 and 8 the relative phases of the respective signals feeding the antenna elements are varied in such a manner that the effective radiation power of the phased-array is reinforced in a specific internal area of the user's body, for example in the pulmonary tissues of the user 101, and optionally suppressed in other directions. In an equivalent manner, the phases of the received signals from the different antenna elements may be combined to focus the elements on a specific internal location. As described above, reflections from the pulmonary tissue may be calibrated according to the reflections from reference tissues, for example increasing the received reflected power from the muscle-to-lung interface, by increasing the inflate-deflate differential signal on the lung gating. Any or all of the transmission and/or reception of the EM signals can be adjusted jointly or separately to maximize the described lung reflection.

By using multiple transducers the time/space separation may be improved. For example, different antenna elements are designed to be focused on reception and/or transmission in different directions, where the interception of the transmission and reception areas of focus are strongly emphasized respective to other areas, so as to improve isolation from internal weaker signals from strong reflection which may or may not overlap in time.

Optionally, the array of transducers 401 comprises transmitting and intercepting antenna elements. By separating between transmitting and intercepting antenna elements, transmission and reception isolation is increased. The improved isolation increases sensitivity to weaker reflections from inner tissues and/or organs, by reducing the reflections received from layers which are in proximity to the transmitting antenna elements. Reception of strong reflections from the first layers in proximity to the transmitting antenna elements, such as skin and fat, are reduced or eliminated in separated receiving antenna elements, therefore achieving improved sensitivity to weaker signals from deeper layers.

The separation of different reflection according to reflected areas allows overcoming microwave monitoring difficulties. For example, when two or more reflections from different areas are simultaneously, or substantially simultaneously, but overlap in time of reception, physiological phenomenon may be masked for example due to mutual cancellation. Focusing the reception and/or transmission to different areas may isolate the two or more reflections from each other and enable efficient extraction of the physiological phenomenon. Optionally, multiple antenna elements and/or multiple transducers are used to reduce irregularities, such as noises, disturbances and/or interferences, which are intercepted in part of the antenna element and/or transducers. Such irregularities may be an outcome of power source instability, noise-figure changes, and changes in the attenuation of the electromagnetic waves which are caused by fluctuations in the gap between the antenna and the skin. Using multi antenna elements and/or multi transducers allows identifying and/or reducing and/or factoring out noises and disturbances. By separately tracking reflections from different sub areas of the monitored tissue and/or organ, noises and disturbances may be separated, for example by detecting similar irregularities in reflections from different tissues.

In such cases array of transducers 401 may separate the reflection.

The wearable monitoring apparatus 100 may direct some or all of the transducers to capture reflection from a certain tissue or split it over separate tissues or connective tissues.

In some embodiments of the present invention, the wearable monitoring apparatus 100 implements one or more gating techniques for gating the reflected EM waves, for example as described in the co filed Patent Application. Such gating techniques allow synchronizing the monitoring with cyclic physiological processes, such as the breathing cycle and the pace of the heart beats. As described in the co filed Patent Application, the time gating techniques may be used for focusing on reflections from the pulmonary tissue. However, time gating may not separate reflections if the reflections are adjacent to one another on the time axis. Optionally, the spatial separation is improved by beaming the microwave from one transducer and capturing the reflections from another transducer. Optionally, the wearable monitoring apparatus, for example as described in FIGS. 7 and 8, beams EM waves from one of the antenna elements 401 and captures the reflections thereof from one or more other antenna elements. Optionally, the beamed EM waves are directed to form a phased-array antenna with directivity pointing with some angle to the desired reflection 405. In such a manner, the backscattering radiation is scattered in an angle which is relatively wide, for example in relation to the backscattering radiation that is beamed and captured by the same transducer. Optionally, where beams of the transmitting and intercepting transducers do not overlap, reflections resulting from tissue transitions are received off-beam and attenuated. In such a manner, the reflections from the borders of the tissue are not attenuated and the desired reflections are kept in there original intensity.

Optionally, one or more intercepting transducers are focused on the reference tissue while other intercepting transducers are focused on the desired pulmonary tissue. Optionally, two or more different intercepting transducers are focused on one or more reflection points.

As described above, the reflected EM waves may be gated during and/or before the analysis process. Using multiple transmitters, as depicted in FIGS. 7 and 8, may be used for increasing the separation between different reflections which are intercepted by the wearable monitoring apparatus. Optionally, the beams a microwave is a CW, as described above. Optionally, the CW is a chirp in which the frequency increases or decreases with time. In such an embodiment, multiple-antenna-elements may be used to transmit and receive the CWs and still have focusing capabilities. For example, one radiating transducer may distribute its radiation across a wide area while the reception is phased by several transducers. In another example, a phased-array forms several beams which are directed to different locations. Optionally, some or more of the transducers includes phase shifters which are designed to point to the desired location. The positioning of a phase-shifter may be adjusted according to the requirements of the reference chest model. Optionally, the phase-shifter is dynamically adjusted according to the analysis of the received reflections. For example, the phase-shifter may be directed to intercept a fat-to-muscle reflection by identifying a strong pass and an opposite-signed reflection from muscle-to-lung.

Optionally, phase-shifters are used for maximizing the amplitude of the waveform of the received reflections. The waveform variance may be affected by the breathing cycle and/or by the dielectric changes of the pulmonary tissue. For example, the phase-shifters are used for maximizing the amplitude of periodic signals such as the signal that reflects the breathing process or the heart beating process.

The intensification of the waveform variance may be used for emphasizing in the small changes in the dielectric coefficients of the pulmonary tissue and for focusing the beam on the pulmonary tissue and/or on lungs transitions. Maximizing the waveform variance resulting from breathing cycles may be measured by correlating between the received reflections and separate measurements of the monitored user breathing.

In some embodiments of the present invention, the wearable monitoring apparatus 100 is adjusted according to the physical and anatomical condition and/or medical history of the monitored user. Optionally, the configuration is performed, either automatically and/or manually, after the wearable monitoring apparatus 100 is attached to user's body. Optionally, a configuration process is associated with the initial placement of the wearable monitoring apparatus 100. The automatic configuration may be based on measurements which are preformed in real time. Optionally a semi-manual configuration process is used where the user and/or the treating caretaker are required to enter medical data and/or to select a monitoring pattern and\or define various thresholds for notifications of either the medical treating team and/or the user. Optionally, the area of the receiving and/or transmitting element may be adapted to the physiology of the user. If the user has relatively thick layers of fat, larger antenna element or elements may be used in order to increase the sensitivity and the effective monitoring range. Optionally, the transducer may be defined to transmit more energy in order to improve the sensitivity of the wearable monitoring apparatus.

Reference is now made, once again, to FIG. 2. In some embodiments of the present invention, a management node, such as the medical data center 155 and/or the patient management unit allows the production of statistical reports, such as financial and/or usage related reports. In such an embodiment the data about the risks and/or the medical condition of the users may be combined with billing and/or accounting data which is related to the user. The medical data center 155 may contain usage and/or statistics data that may be accessed by administrative system users for billing, auditing and the like. For example, a medical insurance company may use usage statistics to ensure that user comply with medical treatment instructions they receive and/or with a requirement to wear the wearable monitoring apparatus 100.

Optionally, the system 150 may be integrated with a medical data system, such as a radiology information system (RIS), an electronic medical record (EMR), and/or a personal health record (PHR). In such an embodiment, the system 150 may streaming the aforementioned data about the monitored users to the medical data system. Optionally, the integration may support records, in standards such as health level 7 (HL7), general electric (GE) EMR format, EPIC EMR format, and Google™ health format. In such an embodiment, data which is related to the placement of the wearable monitoring apparatus and/or any other wearable biological probe may be used for updating insurance rate and/or in a manner that improves patient compliance rates.

Optionally, the system 150 may include a device identification module which is configured for Identifying a match between the outputs of a certain wearable monitoring apparatus 100 and the monitored user that wears it. Such identification may be used for preventing from outputs of a device that is worn by a first user to be associated with records which related to a second user. For example, the wearable monitoring apparatus 100 may identify the user using characteristics of the measured signal unique to him. In the case of a mismatch the system will alert.

Optionally, the system 150 may include a device authorization and activation module which is configured for identifying and authenticating a device before it is allowed to be connected to the system and/or activated and/or enabled for activation. Authentication can be based on unique information stored in the wearable monitoring apparatus 100, Authentication information may be valid for a limited duration and/or number of activations. Such a module reduces fraud where a non-original wearable monitoring apparatus is used within the system.

It is expected that during the life of a patent maturing from this application many relevant methods and systems will be developed and the scope of the term a microwave, a transmitter, a receiver, and/or a device are intended to include all such new technologies a priori.

As used herein the term "about" refers to ±10%.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A wearable monitoring apparatus for monitoring at least one biological parameter of an internal tissue of an ambulatory user, comprising:
at least one transducer having at least one antenna configured for at least one of delivering radio frequency radiation having a plurality of different frequencies between 900 MHz and 2.5 GHz to the internal tissue and intercepting said radio frequency radiation from said internal tissue, in a plurality of transmission sessions during a period of at least 24 hours;
a processing unit configured for:
analyzing said intercepted radio frequency radiation and identifying at least one biological parameter according to a differential signal, to detect a medical condition of the ambulatory user; and
computing the differential signal from a plurality of signals of the intercepted radio frequency radiation based on electromagnetic (EM) radiation obtained over at least one of a breathing cycle and a heartbeat cycle, wherein the differential signal is computed as at least one of:
(i) differences between the intercepted radio frequency radiation received during inspiratory phase and the intercepted radio frequency radiation received during expiratory phase of the breathing cycle, and
(ii) differences between the intercepted radio frequency radiation received during a systolic phase and the intercepted radio frequency radiation received during a diastolic phase of the heartbeat cycle; and
reporting unit configured for generating a report according to said differential signal.

2. The wearable monitoring apparatus of claim 1, wherein said processing unit comprises a communication module for communicating with a remote processing unit thereby allowing performing of at least one of said analyzing and said identifying by said remote processing unit.

3. The wearable monitoring apparatus of claim 1, wherein said processing unit is configured for identifying said at least one biological parameter by detecting at least one of a trend, a biological process, and a pattern according to said intercepted radio frequency radiation of said plurality of transmission sessions.

4. The wearable monitoring apparatus of claim 1, wherein said processing unit is configured for evaluating a property change in a dielectric related property of the internal tissue in at least one of said plurality of transmission sessions and performing said identification according to said property change.

5. The wearable monitoring apparatus of claim 1, wherein said plurality of transmission sessions are performed in an adaptive rate.

6. The wearable monitoring apparatus of claim 5, wherein said adaptive rate is determined according to a clinical state of the user, said processing unit being configured for calculating said clinical state according to at least one output of a non radio frequency radiation sensor and said intercepted radio frequency radiation.

7. The wearable monitoring apparatus of claim 5, further comprising a posture detection unit configured for detecting a posture of the user, said adaptive rate being determined according to said posture.

8. The wearable monitoring apparatus of claim 1, wherein said reporting unit is configured for generating said report in real time.

9. The wearable monitoring apparatus of claim 1, wherein said at least one biological parameter is indicative of a fluid content in the internal tissue during said period.

10. The wearable monitoring apparatus of claim 9, wherein said processing unit is configured for detecting a pattern of at least one physiological activity of the user, said processing unit being configured for calculating a clinical state of said user with respect to said fluid content and to said pattern;
wherein said at least one intercepted radio frequency radiation is being changed as an outcome of at least one thoracic movement during said period.

11. The wearable monitoring apparatus of claim 1, wherein said at least one biological parameter is indicative of a member of a group consisting of: a trauma a degenerative process, atelectasis, a post-operative atelectasis, an acute respiratory deficiency syndrome (ARDS), an infectious cause, an inhaled toxins, a circulating exogenous toxins, a vasoactive substance, a disseminated intravascular coagulopathy (DIC), a burn, an emphysema, a immunologic processes reaction, a uremia, a post drowning lung water level, a pulmonary venous thrombosis, a stenosis, a veno-occlusive disease, a hypoalbuminemia, a lymphatic insufficiency, a high altitude pulmonary edema (HAPE), a neurogenic pulmonary edema, a drug overdose, a pulmonary embolism, an eclampsia, a postcardioversion, a postanesthetic, a postextubation, a post-cardiopulmonary bypass an inflammation progress of ARDS users, and postoperative atelectasis.

12. The wearable monitoring apparatus of claim 1, further comprising a repository configured for storing information pertaining to said user, said processing unit being configured for performing said analyzing with respect to said information, wherein said information comprises at least one of physiological, anatomical, and clinical data related to said user.

13. The wearable monitoring apparatus of claim 1, further comprising a non radio frequency radiation sensor configured for evaluating an indicator of the physical condition of said user, said processing unit identifying said at least one biological parameter by a combination of said indicator and said intercepted radio frequency radiation.

14. The wearable monitoring apparatus of claim 1, further comprising a non EM radiation sensor configured for evaluating an indicator to allow performing said analyzing with respect to said evaluated indicator, said non EM radiation sensor being a member of a group consisting of electromyogram (EMG), an ultrasound transducer, a blood pressure sensor, an optical blood saturation detector, a pulse oximeter, electrocardiogram (ECG), tiltmeter, accelerometer, an activity sensor, and a coagulometer.

15. The wearable monitoring apparatus of claim 1, further comprising a non EM radiation sensor configured for detecting a pattern of a physiological activity of the user, said processing unit being configured for performing said analyzing with respect to said pattern.

16. The wearable monitoring apparatus of claim 1, wherein said processing unit is configured for detecting a pattern of a physiological activity of the user, said processing unit being configured for performing said analyzing with respect to said pattern.

17. The wearable monitoring apparatus of claim 1, wherein said processing unit is configured for detecting a physiological activity of the user by analyzing said intercepted radio frequency radiation, said processing unit being configured for performing said identifying with respect to said physiological activity.

18. The wearable monitoring apparatus of claim 1, further comprising a posture detection unit configured for detecting a posture of the user, said processing unit being configured for analyzing said intercepted radio frequency radiation with respect to said posture.

19. The wearable monitoring apparatus of claim 1, wherein said at least one biological parameter is indicative of a concentration of a solute in the internal tissue.

20. The wearable monitoring apparatus of claim 19, wherein said solute is a member of a group consisting of a salt, glucose, and inflammatory indicative fluid.

21. The wearable monitoring apparatus of claim 1, wherein the processing unit is further configured for detecting the at least one of the breathing cycle and the heartbeat cycle of the patient according to an analysis of the plurality of signals of the intercepted radio frequency radiation.

\* \* \* \* \*